United States Patent
Pearlman et al.

(10) Patent No.: US 9,422,580 B2
(45) Date of Patent: *Aug. 23, 2016

(54) METHODS FOR BIOSYNTHESIZING 1,3 BUTADIENE

(71) Applicant: INVISTA North America S.á r.l., Wilmington, DE (US)

(72) Inventors: Paul S. Pearlman, Thornton, PA (US); Changlin Chen, Ingleby Barwick (GB); Adriana Leonara Botes, Rosedale East (GB); Alex Van Eck Conradie, Eaglescliffe (GB)

(73) Assignee: INVISTA NORTH AMERICA S.A.R.L., Wilmington, DE (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/916,156

(22) Filed: Jun. 12, 2013

(65) Prior Publication Data

US 2014/0141482 A1    May 22, 2014

Related U.S. Application Data

(63) Continuation-in-part of application No. 13/691,623, filed on Nov. 30, 2012, which is a continuation-in-part of application No. 13/524,973, filed on Jun. 15, 2012.

(51) Int. Cl.
  *C12N 9/88* (2006.01)
  *C12P 5/02* (2006.01)
  *C12N 9/02* (2006.01)

(52) U.S. Cl.
  CPC ............... *C12P 5/026* (2013.01); *C12N 9/001* (2013.01); *C12N 9/88* (2013.01); *C12Y 103/08* (2013.01); *C12Y 401/01033* (2013.01); *C12Y 402/01* (2013.01); *C12Y 402/03027* (2013.01); *Y02E 50/343* (2013.01); *Y02P 20/52* (2015.11)

(58) Field of Classification Search
  None
  See application file for complete search history.

(56) References Cited

U.S. PATENT DOCUMENTS

| | | |
|---|---|---|
| 8,703,455 B2 | 4/2014 | Marliere |
| 8,741,612 B2 | 6/2014 | Campbell et al. |
| 2011/0165644 A1 | 7/2011 | Marliere |
| 2011/0300597 A1 | 12/2011 | Burk et al. |
| 2012/0021478 A1 | 1/2012 | Osterhout et al. |
| 2012/0122563 A1 | 5/2012 | Walker et al. |
| 2012/0225466 A1 | 9/2012 | Burk et al. |
| 2013/0189753 A1 | 7/2013 | Pearlman et al. |
| 2013/0210104 A1 | 8/2013 | Pearlman et al. |
| 2013/0309742 A1 | 11/2013 | Campbell et al. |
| 2014/0065686 A1 | 3/2014 | Marliere |
| 2014/0186913 A1 | 7/2014 | Botes et al. |
| 2015/0037860 A1 | 2/2015 | Botes et al. |
| 2015/0079654 A1 | 3/2015 | Botes et al. |

FOREIGN PATENT DOCUMENTS

| | | |
|---|---|---|
| EP | 2336340 A1 | 6/2011 |
| EP | 2336341 A1 | 6/2011 |
| WO | WO2009155382 A1 | 12/2009 |
| WO | WO2010001078 | 1/2010 |
| WO | WO2010099201 A1 | 9/2010 |
| WO | WO2011/011689 | 1/2011 |
| WO | WO 2011/076261 | 6/2011 |
| WO | WO 2011/076689 | 6/2011 |
| WO | WO 2011/076691 | 6/2011 |
| WO | WO 2011/079314 | 6/2011 |
| WO | WO2011140171 A2 | 11/2011 |
| WO | WO2012018624 A2 | 2/2012 |
| WO | WO 2012/052427 | 4/2012 |
| WO | WO2012174439 A2 | 12/2012 |
| WO | WO 2013/007786 | 1/2013 |
| WO | WO 2013/020118 | 2/2013 |
| WO | WO 2013/028519 | 2/2013 |
| WO | WO 2013/040383 | 3/2013 |
| WO | WO2013036812 | 3/2013 |
| WO | WO 2013/057194 | 4/2013 |
| WO | WO 2013/090915 | 6/2013 |
| WO | WO 2013/092567 | 6/2013 |
| WO | WO2013082542 A2 | 6/2013 |
| WO | WO 2013/150100 | 10/2013 |
| WO | WO 2013/173437 | 11/2013 |
| WO | WO 2013/181647 | 12/2013 |
| WO | WO 2013/192183 | 12/2013 |
| WO | WO2013188546 | 12/2013 |
| WO | WO 2014/001517 | 1/2014 |
| WO | WO 2014/033129 | 3/2014 |
| WO | WO 2014/064198 | 5/2014 |
| WO | WO 2014/085612 | 6/2014 |
| WO | WO 2014/015210 | 11/2014 |

OTHER PUBLICATIONS

Barta et al., "Structural basis for nucleotide binding and reaction catalysis in mevalonate diphosphate decarboxylase," Biochemistry, 51(28):5611-5621, Epub Jul. 6, 2012.
Becker et al., "Metabolic flux engineering of L-lysine production in Corynebacterium glutamicum—over expression and modification of G6P dehydrogenase," Journal of Biotechnology, 132(2):99-109, Epub Jun. 6, 2007.
Brigham et al., "Engineering Ralstonia eutropha for Production of Isobutanol from CO2, H2, and O2," Advanced Biofuels and Bioproducts, Chapter 39, 1065-1090, 2012.
Brodkorb et al., "Linalool dehydratase-isomerase, a bifunctional enzyme in the anaerobic degradation of monoterpenes," J Biol Chem., 285(40):30436-30442, Epub Jul. 27, 2010.

(Continued)

*Primary Examiner* — Suzanne M Noakes
*Assistant Examiner* — Jae W Lee
(74) *Attorney, Agent, or Firm* — William J. Simmons; Kathleen A. Tyrrell

(57) ABSTRACT

This document describes biochemical pathways for producing butadiene by forming two vinyl groups in a butadiene synthesis substrate. These pathways described herein rely on enzymes such as mevalonate diphosphate decarboxylase, isoprene synthase, and dehydratases for the final enzymatic step.

35 Claims, 13 Drawing Sheets

(56) References Cited

OTHER PUBLICATIONS

Buckel et al., "Glutaconate CoA-transferase from Acidaminococcus fermentans," Eur J Biochem., 118(2):315-321, Aug. 1981.
Bugg et al., "The emerging role for bacteria in lignin degradation and bio-product formation," Curr Opin Biotechnol., 22 (3):394-400, Epub Nov. 9, 2010.
Chayabutra and Ju, ""Degradation of n-hexadecane and its metabolites by Pseudomonas aeruginosa under microaerobic and anaerobic denitrifying conditions,""Appl Environ Microbiol., 66(2):493-498, Feb. 2000.
Chung and Rhee, "Overexpression of the (R)-specific enoyl-CoA hydratase gene from Pseudomonas chlororaphis HS21 in Pseudomonas strains for the biosynthesis of polyhydroxyalkanoates of altered monomer composition," Biosci. Biotechnol. Biochem., 76(3): 613-616, 2012.
Dhe-Paganon et al., "Mechanism of mevalonate pyrophosphate decarboxylase: evidence for a carbocationic transition state," Biochemistry, 33(45):13355-13362, Nov. 15, 1994.
Eikmanns and Buckel, "Crystalline green 5-hydroxyvaleryl-CoA dehydratase from Clostridium aminovalericum," Eur. J. Biochem., 197(3):661-668, May 8, 1991.
Ferrandez et al., "Genetic characterization and expression in heterologous hosts of the 3-(3-hydroxyphenyl)propionate catabolic pathway of Escherichia coli K-12," J. Bacteriol., 179(8): 2573-2581, Apr. 1997.
Gogerty and Bobik, "Formation of isobutene from 3-hydroxy-3-methylbutyrate by diphosphomevalonate decarboxylase," Appl Environ Microbiol., 76(24):8004-8010, Epub Oct. 22, 2010.
Guan et al., "Cytochrome P450-dependent desaturation of lauric acid: isoform selectivity and mechanism of formation of 11-dodecenoic acid," Chem Biol Interact, 110(1-2):103-121, Mar. 1998.
He and Spain, "A novel 2-aminomuconate deaminase in the nitrobenzene degradation pathway of Pseudomonas pseudoalcaligenes JS45," J Bacteriol., 180(9):2502-2506, May 1998.
Hermann et al, "Industrial production of amino acids by coryneform bacteria," J Biotechnol., 104(1-3):155-172, Sep. 2003.
Jang et al., "Bio-based production of C2-C6 platform chemicals," Biotechnol Bioeng., 109(10):2437-2459, Epub Jul. 13, 2012.
Jaremko and Yu, "The initial metabolic conversion of levulinic acid in Cupriavidus necator," J Biotechnol., 155 (3):293-298, Epub Jul. 30, 2011.
Kasai et al., "Uncovering the protocatechuate 2,3-cleavage pathway genes," J Bacteriol., 191(21):6758-6768, Epub Aug. 28, 2009.
Kim et al., "An allylic ketyl radical intermediate in clostridial amino-acid fermentation," Nature., 452(7184):239-242, Mar. 2008.
Kim, "On the enzymatic mechanism of 2-hydroxyisocaproyl-CoA dehydratase from Clostridium difficile," 2004, Ph.D. dissertation, Philipps-Universität, Marburg, 2004.
Köpke et al., "2,3-butanediol production by acetogenic bacteria, an alternative route to chemical synthesis, using industrial waste gas," Appl Environ Microbiol., 77(15):5467-5475, Epub Jun. 17, 2011.
Kuzma et al., "Bacteria produce the volatile hydrocarbon isoprene," Curr Microbiol., 30(2):97-103, Feb. 1995.
Kuzuyama, "Mevalonate and nonmevalonate pathways for the biosynthesis of isoprene units," Biosci Biotechnol Biochem., 66(8):1619-1627, Aug. 2002.
Lee et al., "Synthesis of pure meso-2,3-butanediol from crude glycerol using an engineered metabolic pathway in Escherichia coli," Appl Biochem Biotechnol., 166(7):1801-1813, Epub Mar. 21, 2012.
Li et al., "Cupriavidus necator JMP134 rapidly reduces furfural with a Zn-dependent alcohol dehydrogenase," Biodegradation, 22(6): 1215-1225, Nov. 2011.
Lim et al., "Amplification of the NADPH-related genes zwf and gnd for the oddball biosynthesis of PHB in an E. coli transformant harboring a cloned phbCAB operon," J Biosci Bioeng., 93(6):543-549, 2002.
Liu et al., "Microbial production of R-3-hydroxybutyric acid by recombinant E. coli harboring genes of phbA, phbB, and tesB," Appl Microbiol Biotechnol., 76(4):811-818, Epub Jul. 4, 2007.
Luo et al., "Production of 3-hydroxypropionic acid through propionaldehyde dehydrogenase PduP mediated biosynthetic pathway in Klebsiella pneumoniae," Bioresour Technol., 103(1):1-6, Epub Oct. 2, 2011.
Martin and Prather, "High-titer production of monomeric hydroxyvalerates from levulinic acid in Pseudomonas putida," J Biotechnol., 139(1):61-67, Epub Sep. 25, 2008.
Meijnen et al., "Improved p-hydroxybenzoate production by engineered Pseudomonas putida S12 by using a mixed-substrate feeding strategy," Appl Microbiol Biotechnol., 90(3):885-893, Epub Feb. 2, 2011.
Mo et al., "Biosynthesis of the allylmalonyl-CoA extender unit for the FK506 polyketide synthase proceeds through a dedicated polyketide synthase and facilitates the mutasynthesis of analogues," J Am Chem Soc., 133(4):976-985, Epub Dec. 22, 2010.
Muraki et al., "Prokaryotic homologs of the eukaryotic 3-hydroxyanthranilate 3,4-dioxygenase and 2-amino-3-carboxymuconate-6-semialdehyde decarboxylase in the 2-nitrobenzoate degradation pathway of Pseudomonas fluorescens strain KU-7," Appl Environ Microbiol., 69(3):1564-1572, Mar. 2003.
Ohashi et al., "Continuous production of lactic acid from molasses by perfusion culture of Lactococcus lactis using a stirred ceramic membrane reactor," J Biosci Bioeng., 87(5):647-654, 1999.
Papanikolaou et al., "Citric acid production by Yarrowia lipolytica cultivated on olive-mill wastewater-based media," Bioresour Technol., 99(7):2419-2428, Epub Jul. 2, 2007.
Pérez-Pantoja et al., "Metabolic reconstruction of aromatic compounds degradation from the genome of the amazing pollutant-degrading bacterium Cupriavidus necator JMP134," FEMS Microbiol Rev., 32(5):736-794, Epub Aug. 7, 2008.
Przybylski et al., "Third-generation feed stocks for the clean and sustainable biotechnological production of bulk chemicals: synthesis of 2-hydroxyisobutyric acid," Energy, Sustainability and Society, 2:11, 2012.
Ramsay et al., "Use of a nylon manufacturing waste as an industrial fermentation substrate," Appl Environ Microbiol., 52(1):152-156, Jul. 1986.
Rettie et al., "CYP4 Isozyme Specificity and the Relationship between co-Hydroxylation and Terminal Desaturation of Valproic Acid," Biochemistry, 34 , 7889-7895 (1995).
Schäfer et al., "Synthesis of short-chain diols and unsaturated alcohols from secondary alcohol substrates by the Rieske nonheme mononuclear iron oxygenase MdpJ.," Appl Environ Microbiol., 78(17):6280-6284, Epub Jun. 29, 2012.
Scherf and Buckel, "Purification and properties of an iron-sulfur and FAD-containing 4-hydroxybutyryl-CoA dehydratase/vinylacetyl-CoA delta 3-delta 2-isomerase from Clostridium aminobutyricum," Eur J Biochem., 215 (2):421-429, Jul. 15, 1993.
Scherf et al., "Succinate-ethanol fermentation in Clostridium kluyveri: purification and characterisation of 4-hydroxybutyryl-CoA dehydratase/vinylacetyl-CoA delta 3-delta 2-isomerase," Arch Microbiol., 161(3):239-245, 1994.
Seedorf et al., "The genome of Clostridium kluyveri, a strict anaerobe with unique metabolic features," Proc Natl Acad Sci U S A., 105(6):2128-2133, Epub Jan. 24, 2008.
Shen et al., "Driving forces enable high-titer anaerobic 1-butanol synthesis in Escherichia coli," Appl Environ Microbiol., 77(9):2905-2915, Epub Mar. 11, 2011.
Silver and Fall, "Characterization of aspen isoprene synthase, an enzyme responsible for leaf isoprene emission to the atmosphere," J Biol Chem., 270(22):13010-13016, Jun. 2, 1995.
Sweeney et al., "Physiologically based pharmacokinetic modeling of 1,3-butadiene, 1,2-epoxy-3-butene, and 1,2:3,4-diepoxybutane toxicokinetics in mice and rats," Carcinogenesis., 18(4):611-625, Apr. 1997.
Tseng et al., "Biosynthesis of chiral 3-hydroxyvalerate from single propionate-unrelated carbon sources in metabolically engineered E. coli," Microb Cell Fact., 9:96, Nov. 27, 2010.

(56) References Cited

OTHER PUBLICATIONS

Tsuge et al., "Molecular characterization and properties of (R)-specific enoyl-CoA hydratases from Pseudomonas aeruginosa: metabolic tools for synthesis of polyhydroxyalkanoates via fatty acid beta-oxidation," Int J Biol Macromol., 31(4-5):195-205, Jan. 2003.
Ulmer et al., "Bacterial production of poly(.beta.-hydroxyalkanoates) containing unsaturated repeating units by Rhodospirillum rubrum," Macromolecules, 27(7):1675-1679, 1994.
Upton and Mckinney, "Role of the methylcitrate cycle in propionate metabolism and detoxification in Mycobacterium smegmatis," Microbiology, 153(Pt 12):3973-3982, Dec. 2007.
van Leeuwen et al., "Fermentative production of isobutene," Appl Microbiol Biotechnol., 93(4):1377-1387, Epub Jan. 11, 2012.
Buckel et al., "2-Hydroxyacyl-CoA dehydratases, a novel family of molybdenum enzymes," J Inorganic Biochemistry, 2003, 96(1):53, 1 page.
Forster-Fromme et al., "Biochemical characterization of isovaleryl-CoA dehydrogenase (LiuA) of Pseudomonas aeruginosa and the importance of liu genes for a functional catabolic pathway of methyl-branched compounds," FEMS Microbiol Lett, 2008, 286(1):78-84.
Genbank accession No. AAD44196.1, Oct. 15, 1999, 1 page.
Genbank accession No. AAG05403.1, Jan. 31, 2014, 2 pages.
Genbank accession No. AAV40818.1, Feb. 4, 2005, 1 page.
Genbank accession No. AAV40819.1, Feb. 4, 2005, 1 page.
Genbank accession No. AAV40820.1, Feb. 4, 2005, 1 page.
Genbank accession No. BAA21816.1, Aug. 19, 1997, 2 pages.
Genbank accession No. BAA92740, Aug. 1, 2007, 2 pages.
Genbank accession No. CAA32465.1, Jul. 26, 1995, 1 page.
Genbank accession No. CAA32466.1, Jul. 26, 1995, 1 page.
Genbank accession No. CAA42196.1, Oct. 16, 1995, 1 page.
Genbank accession No. CAA99573.1, Nov. 14, 2006, 2 pages.
Genbank accession No. NP_746661, Jun. 27, 2013, 2 pages.
International Preliminary Report on Patentability and Written Opinion for PCT/US2012/064407, issued May 13, 2014, 8 pages.
International Preliminary Report on Patentability and Written Opinion for PCT/US2012/067463, issued Jun. 3, 2014, 12 pages.
International Search Report and Written Opinion in Application No. PCT/US2013/072275, mailed Mar. 6, 2014, 12 pages.
International Search Report and Written Opinion in Application No. PCT/US2013/045430, mailed Feb. 3, 2014, 20 pages.
International Search Report in Application No. PCT/US2012/064407, mailed Feb. 7, 2013, 13 pages.
Invitation to pay additional fees and, where applicable, protest fee for PCT/US2013/045430, mailed Nov. 25, 2013, 6 pages.
Kim et al., "Dehydration of ®-2-hydro9xyacyl-CoA to enoyl-CoA in the fermentation of α-amino acids by anaerobic bacteria," FEMS Microbiol Rev, 2004, 28(4):455-468, 14 pages.
Kizer et al., "Application of Functional Genomics to Pathway Optimization for Increased Isoprenoid Production," Applied and Environmental Microbiology, 2008, 74(10):3229-3241.
Lan et al., "ATP drives direct photosynthetic production of 1-butanol in cyanobacterial," PNAS, 2012, 109(16):6018-6023, 6 pages.
Lee et al., "Conversion of beta-methylbutyric acid to beta-hydroxy-beta-methylbutyric acid by Galactomyces reessii," Appl Environ Microbiol, 1997, 63(11):4191-4195, 5 pages.
Li et al., "JMP134 rapidly reduces furfural with a Zn-dependent alcohol dehydrogenase," Biodegradation, 2011, 22(6):1215-1225, 11 pages.
Martin et al., "Engineering a Mevalonate pathway to Escherichia coli for production of terpenoids," Nature Biothechnology, 2003, 21:796-802.
Morone et al., "Increasing diterpene yield with a modular metabolic engineering system in E. coli: comparison of MEV and MEP isoprenoid precursor pathway engineering," Applied Microbiology and Biotechnology, 2010, 85:1893-1906.
Prather et al., "De nova biosynthetic pathways: rational design of microbial chemical factories," 2008, 19:468-474.

Yang et al., "Enhancing production of bio-isoprene using hybrid MVA pathway and isoprene synthase in E. coli," PLoS One, Apr. 2012, 7:1-7.
Zhao et al., "Biosynthesis of isoprene in Escherichia coli via methylerythritol phosphate (MEP) pathway," Applied Microbilogy and Biotechnology, Apr. 2011, 90:1915-1922.
Daniel et al., "Biochemistry of coenzyme B12-dependent glycerol and diol dehydratases and organization of the encoding genes," 1999, FEMS Microbiology Reviews, 22: 553-566.
Fukui et al., "Expression and characterization of ®-specific enoyl coenzyme A hydratase involved in polyhydroxyalkanoate biosynthesis by Aeromonas caviae," J. Bacteriology, Feb. 1998, 180(3):667-673.
Gehret et al., "Terminal alkene formation by the thioesterase of curacin A biosynthesis: structure of a decarboxylating thioesterase," J. of Biological Chem., 2011, 186(16):14445-14454.
Genbank accession No. E1XUJ2.1. Sep. 5, 2012, 2 pages.
Gu et al., "Polyketide Decarboxylative chain Termination Preceded by 0-sulfonation in curacin A Biosynthesis," J. Am. Chemical Soc., Nov. 2009, 131(44):16033-16035.
International Preliminary Report on Patentability in International Application No. PCT/US2013/045430, mailed Dec. 24, 2014, 12 pages.
International Search Report and Written Opinion in Application No. PCT/US2014/048606, mailed Oct. 31, 2014, 19 pages.
International Search Report and Written Opinion in Application No. PCT/US2014/049807, mailed Nov. 5, 2014, 56 pages.
Jin et al., "The selective addition of water to C=C bonds; enzymes are the best chemists," Chem Commun., 2011, 47:2502-2510.
Kelada et al., "Delta-aminolevulinic acid dehydratase genotype and lead toxicity: A Huge Review," Am. J. Epidemiology, 2001, 154(1)1-13.
Luddeke et al. "Geraniol and Geranial Dehydrogenases Induced in Anaerobic Monoterpene Degradation by Castellaniella defragrans," Appl. and Environmental Microbiology, 2012, 78(7): 2128-2136.
Luddeke et al.," Enantiospecific (S)-(+)-linalool formation from beta-myrcene by linalool dehydratase-isomerase," Z Naturforsch C., Jul./Aug. 2011, 66(7-8):409-412.
McCarthy et al., "Structural basis of functional group activation by sulfotransferases in complex metabolic pathways," ACS Chem. Biol., 2012, 7:1994-2003.
Rude et al., "Terminal olefin (1-alkene) biosynthesis by a novel p450 fatty acid decarboxylase from Jeotgalicoccus speciesm," Appl. Environ. Microbiol., 2011, 77(5):1718-1727.
Toraya, "Radical catalysis of B12 enzymes: structure, mechanism, inactivation and reactivation of diol and glycerol dehydratases," Cellular and Molecular Life Sciences, 2000, 57:106-127.
Uniprot Accession No. I3RA72, Sep. 5, 2012, 2 pages.
US Final Office Action in U.S. Appl. No. 13/691,623, mailed Dec. 9, 2014, 15 pages.
US Final Office Action in U.S. Appl. No. 13/524,973, mailed Dec. 22, 2014, 24 pages.
US Non-Final Office Action in U.S. Appl. No. 13/691,623, mailed Jun. 25, 2014, 13 pages.
US Non-Final Office Action in U.S. Appl. No. 13/524,973, mailed Jun. 11, 2014, 17 pages.
US Non-Final Office Action in U.S. Appl. No. 13/092,115, mailed Apr. 1, 2015, 21 pages.
Wang and Liao, "Alteration of product specificity of Rhodobacter sphaeroides phytoene desaturase by directed evolution," J Biol Chem., 276(44):41161-41164, Epub Aug. 28, 2001.
Wee et al., "Biotechnological production of lactic acid and its recent applications," Food Technol. Biotechnol., 44(2): 163-172, 2006.
Wendt et al., "Crystal structure of the carboxyltransferase subunit of the bacterial sodium ion pump glutaconyl-coenzyme A decarboxylase," EMBO J., 22(14):3493-3502, Jul. 15, 2003.
White, "Butadiene production process overview," Chem Biol Interact., 166(1-3):10-14, Epub Jan. 26, 2007.
Yang et al., "Value-added uses for crude glycerol—a byproduct of biodiesel production," Biotechnology for Biofuels, 5:13, Mar. 14, 2012.
Uniprot Accession No. P32377, Jun. 15, 2010, 4 pages.
Uniprot Accession No. Q7CCL9, Jun. 15, 2010, 2 pages.

(56) References Cited

OTHER PUBLICATIONS

Uniprot Accession No. B8ZLF3, Jun. 15, 2010, 2 pages.
International Preliminary Report on Patentability and Written Opinion for PCT/US2012/042757, issued Dec. 17, 2013, 7 pages.
International Search Report in Application No. PCT/US2012/042757 mailed Mar. 6, 2013, 5 pages.
International Search Report in Application No. PCT/US2012/067463, mailed Jun. 17, 2013, 19 pages.
Invitation to pay additional fees and, where applicable, protest fee for PCT/US2012/067463, mailed Mar. 13, 2013, 17 pages.
Akatsuka et al., "The Serratia marcescens bioH gene encodes an esterase," GENE, Jan. 2003, 302:185-192.
Eriksen et al., "Protein Design for Pathway Engineering," Journal of Structural Biology, Apr. 2013, 185(2):234-242.
Invitation to pay additional fees and, where applicable, protest fee for PCT/US2015/036095, mailed Sep. 18, 2015, 13 pages.
Lin et al., "The BioC O-Methyltransferase Catalyzed Methyl Esterification of Malonyl-Acyl Carrier Protein, an Essential Step in Biotin Synthesis," Journal of Biological Chemistry, Sep. 2012, 287(44):37010-37020.
Lin et al., "Biotin Sythesis Begins by Hijacking the Fatty Acid Synthetic Pathway," Nature Chem Biol., Sep. 2010, 6:682-688.
Uniprot Accession No. O32472, Jun. 11, 2014, 2 pages.
Uniprot Accession No. P0A6RO, May 14, 2014, 5 pages.
Uniprot Accession No. P0A8Z0, Jun. 11, 2014, 3 pages.
Uniprot Accession No. P0AGG2, Jun. 11, 2014, 3 pages.
Uniprot Accession No. P0AEK4, Jun. 11, 2014, 6 pages.
Uniprot Accession No. P0A6Q6, Jun. 11, 2014, 3 pages.
Uniprot Accession No. P0A953, Jun. 11, 2014, 4 pages.
Uniprot Accession No. P0AEK2, May 14, 2014, 4 pages.
Uniprot Accession No. P13001, Jun. 11, 2014, 4 pages.
Uniprot Accession No. Q5EU90, Feb. 19, 2014, 2 pages.
Uniprot Accession No. Q73Q47, May 14, 2014, 2 pages.
Uniprot Accession No. Q818X2, Jun. 11, 2014, 2 pages.
US Final Office Action in U.S. Appl. No. 14/092,115, mailed Oct. 27, 2015, 8 pages.
Westin et al., "The identification of a succinyl-CoA thioesterase suggests a novel pathway for succinate production in peroxisomes," J. Biol Chem, 2005, 280:38125-38132.
Chinese Office Action in Chinese Application No. 201280040122.2, dated Jul. 17, 2015, 7 pages.
International Preliminary Report on Patentability and Written Opinion for PCT/US2013/072275, issued Jun. 2, 2015, 8 pages.
"Production of butadiene," China Synthetic Rubber Industry, Special issue of 1978, 21 pages (with partial English translation).
US Non-Final Office Action in U.S. Appl. No. 13/524,973, mailed Jul. 23, 2015, 24 pages.
Zhang et al., "Genes encoding acyl-CoA dehydrogenase (AcdH) homologues from Streptomyces coelicolor and Streptomyces avermitilis provide insights into the metabolism of small branched-chain fatty acids and macrolide antibiotic production," Microbiology, 1999, 145(9):2323-2334, 12 pages.
Zhuang et al., "Divergence of function in the Hotdog-fold enzyme superfamily: the bacterial thioesterase YciA," Biochemistry, 2008, 47(9):2789-2796, 8 pages.
International Search Report and Written Opinion in Application No. PCT/US2014/049786, mailed Sep. 11, 2015, 17 pages.

| Microorganism | MDD amino acid sequence |
|---|---|
| Saccharomyces cerevisiae | MTVYTASVTAPVNIATLKYWGKRDTKLNLPTNSSISVTLSQDDLRTLTSAATAPEFERDT LWLNGEPHSIDNERTQNCLRDLRQLRKEMESKDASLPTLSQWKLHIVSENNFPTAAGLAS SAAGFAALVSAIAKLYQLPQSTSEISRIARKGSGSSACRSLFGGYVAWEMGKAEDGHDSMA VQIADSSDWPQMKACVLVVSDIKKDVSSTQGMLTVATSELFKERIEHVVPKREVMRKA IVEKDFATFAKETMMDSNSFHATCLDSFPPIFYMNDTSKRIISWCHTINQFYGETIVAYT FDAGPNAVLYYLAENESKLFAFIYKLFGSVPGWDKKFTTEQLEAFNHQFESSNFTARELD LELQKDVARVILTQVGSGPQETNESLIDAKTGLPKE |
| Staphylococcus epidermidis | MVKSGKARAHTNIALIKYWGKADETYIIPMNNSLSVTLDRFYTETKVTFDPDFTEDCLIL NGNEVNAKEKEIQNYMNIVRDLAGNRLHARIESENYVPTAAGLASSASAYAALAAACNE ALSLNLSDTDLSRLARRGSGSASRSIFGGFAEWEKGHDDLTSYAHGINSNGWEKDLSMIF VVINNQSKKVSSRSGMSLTRDTSRFYQYWLDHVDEDLNEAKEAVKNQFQRLGEVIEANG LRMHATNLGAQPPFTYLVQESYDAMAIVEQCRKANLPCYFTMDAGPNVKVLVEKKNKQAV MEQFLKVFDESKIIASDIISSGVEIIK |
| Streptococcus pneumonia | MDREPVTVRSYANIAIIKYWGKKKEKEMVPATSSISLTLENMYTETTLSPLPANVTADEF YINGQLQNEVEHAKMSKIIDRYRPAGEGFVRIDTQNNMPTAAGLSSSSGLSALVKACNA YFKLGLDRSQLAQEAKFASGSSSSRSFYGPLGAWDKDSGEIYPVETDLKLAMIMLVLEDKK KPISSRDGMKLCVETSTTFDDWVRQSEKDYQDMLIYLKENDFAKIGELTEKNALAMHATT KTASPAFSYLTDASYEAMDFVRQLREKGEACYFTMDAGPNVKVFCQEKDLEHLSEIFGHR YRLLIVSKTKDLSQDCC |

METHODS FOR BIOSYNTHESIZING 1,3 BUTADIENE

CROSS-REFERENCES TO RELATED APPLICATIONS

The present application is a continuation-in-part of co-pending U.S. application Ser. No. 13/691,623, filed Nov. 30, 2012, which is a continuation-in-part of U.S. application Ser. No. 13/524,973, filed Jun. 15, 2012, which claims the benefit of U.S. Provisional Application No. 61/498,408, filed Jun. 17, 2011, all of which are incorporated herein by reference in their entirety.

TECHNICAL FIELD

This invention relates to methods for biosynthesizing 1,3-butadiene, and more particularly to synthesizing 1,3-butadiene using one or more isolated enzymes such as dehydrogenases, monooxygenases, desaturases, dehydratases, and decarboxylases, or using recombinant host cells expressing one or more of such enzymes.

BACKGROUND 1,3-Butadiene (hereinafter butadiene) is an important monomer for the production of synthetic rubbers including styrene-butadiene-rubber (SBR), polybutadiene (PB), styrene-butadiene latex (SBL), acrylonitrile-butadiene-styrene resins (ABS), nitrile rubber, and adiponitrile, which is used in the manufacture of Nylon-66 (White, Chemico-Biological Interactions, 2007, 166, 10-14).

Butadiene is typically produced as a co-product from the steam cracking process, distilled to a crude butadiene stream, and purified via extractive distillation (White, Chemico-Biological Interactions, 2007, 166, 10-14).

On-purpose butadiene has been prepared among other methods by dehydrogenation of n-butane and n-butene (Houdry process); and oxidative dehydrogenation of n-butene (Oxo-D or O-X-D process) (White, Chemico-Biological Interactions, 2007, 166, 10-14).

Industrially, 95% of global butadiene production is undertaken via the steam cracking process using petrochemical-based feedstocks such as naphtha. Production of on-purpose butadiene is not significant, given the high cost of production and low process yield (White, Chemico-Biological Interactions, 2007, 166, 10-14).

Given a reliance on petrochemical feedstocks and, for on-purpose butadiene, energy intensive catalytic steps; biotechnology offers an alternative approach via biocatalysis. Biocatalysis is the use of biological catalysts, such as enzymes, to perform biochemical transformations of organic compounds.

Accordingly, against this background, it is clear that there is a need for sustainable methods for producing intermediates, in particular butadiene, wherein the methods are biocatalyst based (Jang et al., Biotechnology & Bioengineering, 2012, 109(10), 2437-2459).

Both bioderived feedstocks and petrochemical feedstocks are viable starting materials for the biocatalysis processes.

The generation of two vinyl groups into medium carbon chain length enzyme substrates is a key consideration in synthesizing butadiene via biocatalysis processes.

There are no known enzyme pathways leading to the synthesis of butadiene in prokaryotes or eukaryotes. Three potential pathways have been suggested for producing 1,3-butadiene from biomass-sugar: (1) from acetyl-CoA via crotonyl-CoA; (2) from erythrose-4-phosphate; and (3) via a condensation reaction with malonyl-CoA and acetyl-CoA. However, no information using these strategies has been reported (Jang et al., Biotechnology & Bioengineering, 2012, 109(10), 2437-2459).

The closest analogous compound synthesized by prokaryotes or eukaryotes is 2-methyl-1,3-butadiene (isoprene), given the short five carbon chain length and two vinyl groups. Isoprene may be synthesised via two routes leading to the precursor dimethylvinyl-PP, viz. the mevalonate and the non-mevalonate pathway (Kuzuyama, Biosci. Biotechnol. Biochem., 2002, 66(8), 1619-1627).

The mevalonate pathway incorporates a decarboxylase enzyme, mevalonate diphosphate decarboxylase (hereafter MDD), that generates the first vinyl-group in the precursors leading to isoprene (Kuzuyama, Biosci. Biotechnol. Biochem., 2002, 66(8), 1619-1627).

Mevalonate diphosphate decarboxylase (EC 4.1.1.33) may thus be earmarked as a candidate enzyme in the synthesis of butadiene from non-native substrates.

In elucidating the role of the 3-methyl group associated with the native substrate, mevalonate diphosphate, it has been demonstrated that the turn-over number, $k_{cat}$, for 3-hydroxy-5-diphosphatepentanoic acid as shown in FIG. 12(a) is dramatically lower at $0.23\pm0.05$ [$s^{-1}$] as opposed to the nominal $8.33\pm1$ [$s^{-1}$] for the native substrate (Dhe-Paganon et al., Biochemistry, 1994, 33, 13355-13362). In addition, the reaction with substrate only progressed as far as phosphorylation of the 3-hydroxyl group, i.e., no decarboxylated product was detectable, implying that the decarboxylation rate is decreased at least 300 fold compared to the native substrate. In conclusion, the 3-methyl group was deemed indispensible in stabilizing the carbo-cation transition state (Dhe-Paganon et al., Biochemistry, 1994, 33, 13355-13362).

It has been demonstrated that the MDD enzyme from Saccharomyces cerevisiae accepts 3-hydroxy-3-methyl-butyrate (FIG. 12(b)), which includes the 3-methyl group stabilizing the carbocation transition state, as a substrate converting the substrate to isobutene. However, the specific activity is dramatically lower at $4.8 \cdot 10^{-6}$ [$\mu mol/(min \cdot mg)$] as opposed to the native substrate activity of 6.4 [$\mu mol/(min \cdot mg)$] (Gogerty & Bobik, Applied & Environmental Microbiology, 2010, 76(24), 8004-8010).

The key substrate binding interactions of serine and arginine residues on the periphery of the catalytic cleft with the pyrophosphate group of the native substrate mevalonate diphosphate have been elucidated. Correct substrate orientation within the catalytic cleft is thus important to enzyme activity, which plausibly accounts for the low activity of MDD when accepting 3-hydroxy-3-methyl-butyrate (FIG. 14(b)) as substrate (Barta et al., Biochemistry, 2012, 51, 5611-5621).

The importance of the 3-methyl group and the pyrophosphate group associated with the native substrate in underpinning the activity of MDD teaches against using MDD in the synthesis of butadiene from non-native precursors that do not contain these key groups.

The enzyme, isoprene synthase (hereinafter ISPS), generates the second vinyl group in the final precursor, dimethylvinyl-PP, of isoprene synthesis.

Isoprene synthase (EC 4.2.3.27) may thus be earmarked as a candidate enzyme in the synthesis of butadiene from non-native substrates.

Similar to MDD, the 3-methyl group associated with the native substrate dimethylvinyl-PP plays an important role in stabilizing the carbo-cation that has been postulated as a transient intermediate (Silver & Fall, J. *Biol. Chem.*, 1995, 270(22), 13010-13016; Kuzma et al., *Current Microbiology*, 1995, 30, 97-103).

The importance of the 3-methyl group in underpinning the activity of ISPS teaches against using ISPS for the synthesis of butadiene from non-native precursors that do not contain the 3-methyl group.

In addition to MDD and ISPS, microorganisms can generate vinyl groups in metabolites typically via dehydratase, ammonia lyase, desaturase, or decarboxylase activity. However, these enzyme activities rarely catalyse the formation of terminal vinyl groups. Dehydratases and ammonia lyases typically accept fatty acid analogues that have activated hydrogen atoms or aromatic compounds, where the aromatic ring serves as an electron withdrawing group. Desaturases predominate in fatty acid synthesis, generating unsaturated bonds at fixed non-terminal positions along long chain fatty acids. In turn, decarboxylases acting on the terminal carboxyl group typically leave the associated alpha functional group at the terminal position after catalysis. Therefore, the associated enzymatic activity of these enzymes teaches against their use for the generation of terminal vinyl groups in short or medium chain carbon metabolites leading to the synthesis of butadiene.

SUMMARY

This document is based at least in part on the discovery that it is possible to construct biochemical pathways for producing medium chain carbon metabolites, in which two vinyl groups can be formed, leading to the synthesis of butadiene. These pathways described herein rely on enzymes such as MDD, ISPS and dehydratases for the final enzymatic step.

Prior to the inventors' surprising discovery, it was not known that enzymes capable of forming two terminal vinyl groups in a medium chain carbon metabolite existed or could be produced for the synthesis of butadiene.

Thus, in one aspect, this document provides enzymes that can convert butadiene synthesis substrates into butadiene. As used herein, the term "butadiene synthesis substrate" refers to a substrate for which an enzyme can catalyze a reaction that results directly in 1,3-butadiene or in a product that, after one or more enzyme-catalyzed reactions, is converted to 1,3-butadiene.

In some embodiments, the first vinyl group leading to the synthesis of butadiene is enzymatically formed in 4-oxalocrotonate, 2-hydroxymuconate semialdehyde, or 2-hydroxy-6-oxonona-2,4-diene-1,9-dioate to produce 2-oxopent-4-enoate. See, FIG. 2.

In some embodiments, the first vinyl group leading to the synthesis of butadiene is enzymatically formed in propanoyl-CoA, lactoyl-CoA, or 3-hydroxypropionyl-CoA to produce propenoyl-CoA. See, FIG. 3.

In some embodiments, the first vinyl group leading to the synthesis of butadiene is enzymatically formed in (R) 3-hydroxy-pentanoate to produce 3-hydroxypent-4-enoate. See, FIG. 4.

In some embodiments, the first vinyl group leading to the synthesis of butadiene is enzymatically formed in pent-2-enoyl [acp] to produce 2,4-pentadienoyl-[acp]. See FIG. 5.

In some embodiments, the first vinyl group leading to the synthesis of butadiene is enzymatically formed in 5-hydroxypentanoyl-CoA (via 5-hydroxy-pent-2-enoyl-CoA as intermediate) or pent-3-enoyl-CoA to produce 2,4-pentadienoyl-CoA. See, FIG. 6.

In some embodiments, the first vinyl group leading to the synthesis of butadiene is enzymatically formed in 4-hydroxybutyryl-CoA, (R) 3-hydroxybutanoyl-CoA or glutaconyl-CoA to produce crotonyl-CoA. See, FIG. 7.

In some embodiments, the first vinyl group leading to the synthesis of butadiene is enzymatically formed in 2-butanol to produce 3-buten-2-ol. See, FIG. 8.

In some embodiments, the second vinyl group leading to the synthesis of butadiene is formed by mevalonate diphosphate decarboxylase (MDD), an enzyme classified under EC 4.1.1.33 (FIG. 9). For example, 2-hydroxypent-4-enoate is converted consecutively by two or more enzymes; producing butadiene in the last enzymatic conversion by decarboxylation directly (FIG. 1, reaction X).

In some embodiments, the second vinyl group leading to the synthesis of butadiene is formed by isoprene synthase (ISPS), an enzyme classified under EC 4.2.3.27 (FIG. 10). For example, activated butenols (diphosphoesters) may be generated by one or more enzymes from butenols (FIG. 1, reaction II); producing butadiene in the last enzymatic conversion by dephosphorylation directly (FIG. 1, reaction III).

In some embodiments, the second vinyl group leading to the synthesis of butadiene is formed by a dehydratase enzyme classified in EC 4.2.1.-, such as linalool dehydratase (EC 4.2.1.127), kievitone hydratase (EC 4.2.1.95), oleate hydratase (EC 4.2.1.53) and carotenoid 1,2-hydratase (EC 4.2.1.131) (FIG. 11). Such dehydratases accept hydroxylated substrates such as butenols. For example, butenols may be generated in one or more enzymatic steps from butanediols, butanols, butenes, butenals or C5 alkenols (FIG. 1, reactions IV, V, VI, VII, IX) by dehydratase, hydratase, desaturase, dehydrogenase or decarboxylase activity; producing butadiene in the last enzymatic conversion by dehydration directly (FIG. 1, reaction I). Butenols include, for example, 1-buten-1-ol, 2-buten-1-ol and 3-buten-2-ol (see FIG. 1).

For example, this document provides enzymes that convert butenols into butadiene. This conversion can be performed by a single enzyme, or may be performed by two or more enzymes, acting sequentially (that is to say, for example, a first enzyme acts on a four carbon molecule to produce a first butenol, and that first butenol then is acted upon by a second enzyme to produce butadiene) (see, e.g., FIG. 1, reaction I).

This document also provides methods of producing butadiene from a unsaturated hydroxylated four carbon molecule, comprising at least one biocatalytic step. For example, the butenol can be activated to the corresponding butenol diphosphoester before conversion to butadiene (see, e.g., FIG. 1, reactions II & III). In some embodiments, the butenol is selected from the group consisting of 1 buten 2 ol, 1 buten 3 ol, 1 buten 4 ol, 2 buten 1 ol, 2 buten 2 ol, 2 buten 3 ol or 2 buten 4 ol. For butenol such as 1-buten-1-ol, 1-buten-2-ol, 2-buten-2-ol, and 2-buten-3-ol the butenol can be generated in situ as the enolate of the corresponding ketone or aldehyde such as 1-butanal or 2-butanone.

In some embodiments, a butenol is produced from four carbon molecules selected from the group consisting of a butanediol (1,4-butanediol, 1,3-butanedio-1,2,3-butanediol) (FIG. 1, reaction IV) or a butanol (1-butanol, or 2-butanol) (FIG. 1, reaction V) or a butene (1-butene or 2-butene) (FIG. 1, Reaction VI) or a butenal such as 1-butenal or 2-butenal, or a 2-keto-but-1-ene (FIG. 1, reaction VII) by the action of an enzyme.

The reactions performed by the enzymes can be net dehydration (i.e., the removal of $H_2O$ from the molecule by an enzyme having dehydratase activity, reaction IV), dehydrogenation (i.e., the removal of hydrogen from the molecule, which in the reactions catalysed by the enzymes results in a desaturation of the carbon backbone of the molecule) by an enzyme or enzyme complex having desaturase activity, reaction V), hydroxylation (i.e., the replacement of a hydrogen with a hydroxyl group) by an enzyme with hydroxylase activity, such as an alkene monooxygenase or Cytochrome P450 or ω-hydroxylase (reaction VI), or reduction by an oxidoreductase/ketone reductase to convert butenals or C4 unstaurated ketones to butenols. For the dehydration step, the enzyme may be the same enzyme class as the enzyme class used for the dehydration of the butenol to butadiene or may be of another enzyme class. Migration of the double bond in the butenols may be catalysed by isomerases.

This document also provides an enzyme from the enzyme class 4.2.1.-. which converts butanediols to butenol (FIG. 1, reaction VIII).

In some embodiments, a butenol such as 1-buten-4-ol is produced from a five carbon molecule such as 2-hydroxypent-4-enoate by the action of a decarboxylase (such as a decarboxylase from EC 4.1.1.-) (FIG. 1, reaction IX). 2-hydroxypent-4-enoate may also be converted directly into butadiene by a decarboxylase or GHMP kinase without formation of the intermediate butenol (FIG. 1, Reaction X).

In some embodiments, the butenol is selected from the group consisting of 1 buten 2 ol, 1 buten 3 ol, 1 buten 4 ol, 2 buten 1 ol, 2 buten 2 ol, 2 buten 3 ol or 2 buten 4 ol. For butenol such as 1-buten-2-ol, 2-buten-2-ol, and 2-buten-3-ol the butenol can be generated in situ as the enolate of the corresponding ketone or aldehyde such as 1-butanal or 2-butanone.

In one aspect, this document features a method for the biosynthesis of butadiene. The method includes forming two terminal vinyl groups in a butadiene synthesis substrate. A first vinyl group can be enzymatically formed in the butadiene synthesis substrate to produce a compound selected from the group consisting of 2-oxopent-4-enoate, propenyl-CoA, (R) 3-hydroxypent-4-enoate, 2,4-pentadienoyl-[acp], 2,4-pentadienoyl-CoA, crotonyl-CoA, and 3-buten-2-ol.

In one aspect, 2-oxopent-4-enoate can be produced by forming a first vinyl group in (i) 4-oxalocrotonate using an 4-oxalocrotonate decarboxylase classified in EC 4.1.1.77, (ii) 2-hydroxymuconate semialdehyde using a 2-hydroxymuconate-semialdehyde hydrolase classified in EC 3.7.1.9, or (iii) 2-hydroxy-6-oxonona-2,4-diene-1,9-dioate using a 2-hydroxy-6-oxonona-2,4-dienedioate hydrolase classified in EC 3.7.1.14. 2-oxopent-4-enoate can be produced by converting 2-hydroxymuconate semialdehyde to 2-hydroxymuconate using a 2 aminomuconate semialdehyde dehydrogenase classified under EC 1.2.1.32, converting 2-hydroxymuconate to 4-oxalocrotonate using a 2-hydroxymuconate tautomerase classified under EC 5.3.2.6, and converting 4-oxalocrotonate to 2-oxopent-4-enoate using a 4-oxalocrotonate decarboxylase classified under EC 4.1.1.77. 2-hydroxymuconate semialdehyde can be produced by converting catechol to 2-hydroxymuconate semialdehyde using a catechol 2,3-dioxygenase classified under EC 1.13.11.2. Catechol is produced by converting anthranilate using an anthranilate 1,2-dioxygenase classified under EC 1.14.12.1 or by converting protocatechuate using a protocatechuate decarboxylase classified under EC 4.1.1.63. Anthranilate can be produced by converting chorismate using an anthranilate synthase classified under EC 4.1.3.27. Protocatechuate can be produced by converting 3-dehydroshikimate using a 3-dehydroshikimate dehydratase classified under EC 4.2.1.118.

In one aspect, 2-hydroxymuconate semialdehyde can be produced by converting 5-carboxy-2-hydroxymuconate-6-semiladehyde using a 5-carboxy-2-hydroxymuconate-6-semialdehyde decarboxylase such as a 5-carboxy-2-hydroxymuconate-6-semialdehyde decarboxylase is encoded by praH. The 5-carboxy-2-hydroxymuconate-6-semiladehyde can be produced by converting protocatechuate using a protocatechuate 2,3-dioxygenase such as protocatechuate 2,3-dioxygenase is encoded by praA. 2-hydroxy-6-oxonona-2,4-diene-1,9-dioate can be produced by converting 2,3-dihydroxy phenylpropionoate using a 3-carboxyethylcatechol 2,3-dioxygenase classified under EC 1.13.11.16. 2,3-dihydroxyphenylpropionate can be produced by converting cis-3-(carboxy-ethyl)-3,5-cyclo-hexadiene-1,2-diol using a 3-(cis-5,6-dihydroxycyclohexa-1,3-dien-1-yl) propanoate dehydrogenase classified under EC 1.3.1.87. Cis-3-(carboxy-ethyl)-3,5-cyclo-hexadiene-1,2-diol can be produced by converting 3-phenyl-propionate using a 3-phenylpropanoate dioxygenase classified under EC 1.14.12.19. The 3-phenyl-propionate can be produced by converting E-cinnamate using a 2-enoate reductase classified under EC 1.3.1.31. E-cinnamate can be produced by converting L-phenylalanine using a phenylalanine ammonia-lyase classified under EC 4.3.1.24.

In one aspect, the butadiene synthesis substrate can be propanoyl-CoA. Propenoyl-CoA can be produced by forming a first vinyl group in (i) propanoyl-CoA using a butyryl-CoA dehydrogenase classified under EC 1.3.8.1 or a medium-chain acyl-CoA dehydrogenase classified under EC 1.3.8.7, (ii) lactoyl-CoA using a lactoyl-CoA dehydratase classified under EC 4.2.1.54, or (iii) 3-hydroxypropionyl-CoA using a 3-hydroxypropionyl-CoA dehydratase classified under EC 4.2.1.116. The propanoyl-CoA can be produced by converting (2S)-methylmalonyl-CoA using a methylmalonyl-CoA carboxytransferase classified under EC 2.1.3.1 or a methylmalonyl-CoA decarboxylase classified under EC 4.1.1.41. The (2S)-methylmalonyl-CoA can be produced by converting (2R)-methylmalonyl-CoA using a methylmalonyl-CoA epimerase classified under EC 5.1.99.1. The (2R)-methylmalonyl-CoA can be produced by converting succinyl-CoA using a methylmalonyl-CoA mutase classified under EC 5.4.99.2.

The propanoyl-CoA can be produced by converting 2-oxo-butyrate using a 2-ketobutyrate formate-lyase classified under EC 2.3.1.- such as the 2-ketobutyrate formate-lyase encoded by tdcE. The 2-oxo-butryate can beproduced by converting L-threonine using a threonine ammonia lyase classified under EC 4.3.1.19.

The propanoyl-CoA can be produced by converting propanol using a propionaldehyde dehydrogenase such as a propionaldehyde dehydrogenase is encoded by pduP Propanol can be produced by converting 1,2-propanediol using a propanediol dehydratase classified under EC 4.2.1.28.

The propanoyl-CoA can be produced from levulinic acid by converting levulinyl-CoA using a transferase classified under EC 2.3.1.-. The levulinyl-CoA can be produced by converting levulinyl acid using an acyl-CoA synthetase or ligase classified under EC 6.2. 1.-.

The lactoyl-CoA can be produced by converting L-lactate using a proprionate CoA-transferase classified under EC 2.8.3.1. L-lactate can be produced by converting pyruvate using an L-lactate dehydrogenase classified under EC 1.1.1.27.

The 3-hydroxypropionyl-CoA can be produced by converting 3-hydroxypropionate using a 3-hydroxyisobutyryl-CoA hydrolase classified under EC 3.1.2.4 or by converting malonate semialdehyde using a 3-hydroxypropionate dehydrogenase classified under EC 1.1.1.59. The malonate semi-aldehyde is produced by converting malonyl-CoA using a malonyl-CoA reductase classified under EC 1.2.1.75.

The propanoyl-CoA can be produced by converting propenoyl-CoA using a butyryl-CoA dehydrogenase classified under EC 1.3.8.1 or a medium-chain acyl-CoA dehydrogenase classified under EC 1.3.8.7.

The (R) 3-hydroxypent-4-enoate propenoyl-CoA can be produced by forming a first vinyl in (R) 3-hydroxypentanoate using a desaturase/monooxygenase or cytochrome P450. The (R) 3-hydroxy-pentanoate can be produced by converting (R) 3-hydroxypentanoyl-CoA using a thioesterase classified under EC 3.1.2.-. The (R) 3-hydroxypentanoyl-CoA can be produced by converting 3-oxopentanoyl-CoA using an acetoacetyl-CoA reductase classified under EC 1.1.1.36. The 3-oxopentanoyl-CoA can be produced by converting propanoyl-CoA using an acetyl-CoA C-acyltransferase classified under EC 2.3.1.16.

The 2,4-pentadienoyl-[acp] can be produced by forming a first vinyl group in pent-2-enoyl-acp using an acyl-[acp] dehydrogenase. The 2,4-pentadienoyl-CoA can be produced by forming a first vinyl group in (i) 5-hydroxypentanoyl-CoA using a 5-hydroxyvaleryl-CoA dehydratase classified under EC 4.2.1.- or (ii) pent-3-enoyl-CoA using a 2,4-dienoyl coenzyme A reductase classified under EC 1.3.1.34. The 5-hydroxyvaleryl-CoA dehydratase can originate from *Clostridium viride*.

The crotonyl-CoA can be produced by forming a first vinyl group in (i) glutaconyl-CoA using a glutaconyl-CoA decarboxylase classified under EC 4.1.1.70, (ii) 4-hydroxybutryl-CoA using a 4-hydroxybutanoyl-CoA dehydratase classified under EC 4.2.1.120 and a vinylacetyl-CoA isomerase classified under EC 5.3.3.3, or (iii) (R) 3-hydroxybutanoyl-CoA using an enoyl-CoA hydratase classified under EC 4.2.1.119.

The 3-buten-2-ol can be produced by forming a first vinyl group in 2-butanol using a desaturase or a monooxygenase.

The second vinyl group is enzymatically formed in (R) 3-hydroxypent-4-enoate by a mevalonate diphosphate decarboxylase (MDD). The MDD can be classified under EC 4.1.1.33. The MDD can include a minimum of four serine residues within five residues either side of the catalytic arginine residue of the catalytic cleft. The MDD can be from the genus *Streptococcus* or *Staphylococcus*.

The second vinyl group can be enzymatically formed in either 2-buten-1-ol diphosphate or 3-buten-2-ol diphosphate by an isoprene synthase (ISPS). The second vinyl group can be enzymatically formed in either 3-buten-2-ol or 2-buten-1-ol by a dehydratase in enzyme class EC 4.2.1.- such as a linalool dehydratase (EC 4.2.1.127), a kievitone hydrase (EC 4.2.1.95), an oleate hydratase (EC 4.2.1.53) or a carotenoid 1,2-hydratase (EC 4.2.1.131).

The pent-2-enoyl-[acp] can be produced by converting (R) 3-hydroxypentanoyl-[acp] using a 3-Hydroxyacyl-[acp] dehydratase classified under EC 4.2.1.59. The (R) 3-hydroxypentanoyl-[acp] can be produced by converting 3-oxopentanoyl-[acp] using a 3-oxoacyl-[acp] reductase classified under EC 1.1.1.100.

3-oxopentanoyl-[acp] can be produced by converting propanoyl-CoA using a beta-ketoacyl-[acp] synthase I classified under EC 2.3.1.41 and an acyl-transferase such as tcsA.

The pent-2-enoyl-[acp] can be produced by converting pent-2-enoyl-CoA using an acyl transferase. The pent-2-enoyl-CoA can be produced by converting (R) 3-hydroxypentanoyl-CoA using an enoyl-CoA hydratase classified under EC 4.2.1.119. The (R) 3-hydroxypentanoyl-CoA can be produced by converting 3-oxopentanoyl-CoA using an acetoacetyl-CoA reductase classified under EC 1.1.1.36.

The 3-oxopentanoyl-CoA can be produced by converting propanoyl-CoA using an acetyl-CoA C-acyltransferase classified under EC 2.3.1.16.

The pent-3-enoyl-CoA can be produced by converting pent-2-enoyl-CoA using an isomerase classified under EC 5.3.3.8.

The 5-hydroxypentanoyl-CoA can be produced by converting either (i) 5-hydroxypentanoate using 5-hydroxypentanoate CoA-transferase classified under EC 2.8.3.14 or (ii) pentanoyl-CoA using a cytochrome P450 such as the gene product of CYP153A6. The 5-hydroxypentanoate can be produced by converting 5-oxopentanoate using a 5-hydroxyvalerate dehydrogenase such as the gene product of cpnD or the dehydrogenase from *Clostridium viride*. The 5-oxopentanoate can be produced by converting 5-aminovalerate using a 5-aminovalerate transaminase classified under EC 2.6.1.48. The 5-aminovalerate can be produced by converting D-proline using a D-proline reductase classified under EC 1.21.4.1. D-proline can be produced by converting L-proline using a proline racemase classified under EC 5.1.1.4. L-proline can be produced by converting (S)-1-Pyrroline-5-carboxylate using a pyrroline-5-carboxylate reductase classified under EC 1.5.1.2. (S)-1-Pyrroline-5-carboxylate can be produced by spontaneous conversion of L-glutamate 5-semialdehyde. L-glutamate 5-semialdehyde can be produced by converting L-glutamyl-5-phosphate using a glutamate-5-semialdehyde dehydrogenase classified under EC 1.2.1.41. The L-glutamyl-5-phosphate can be produced by converting L-glutamate using glutamate 5-kinase classified under EC 2.7.2.11.

The pentanoyl-CoA can be produced by converting pent-2-enoyl-CoA using a trans-2-enoyl-CoA reductase classified under EC 1.3.1.38.

Glutaconyl-CoA can be produced by converting 2-hydroxyglutaryl-CoA using a dehydratase classified under EC 4.2.1.- The 2-hydroxyglutaryl-CoA can be produced by converting 2-hydroxyglutarate using a glutaconate CoA-transferase classified under EC 2.8.3.12. The 2-hydroxyglutarate can be produced by converting 2-oxoglutarate using a 2-hydroxyglutarate dehydrogenase classified under EC 1.1.99.2. The 3-hydroxybutanoyl-CoA can be produced by converting acetoacetyl-CoA using 3-hydroxybutyryl-CoA dehydrogenase classified under EC 1.1.1.36. The acetoacetyl-CoA can be produced by converting acetyl-CoA using acetyl-CoA C-acetyltransferase classified under EC 2.3.1.9.

The 4-hydroxybutyryl-CoA can be produced by converting 4-hydroxybutyrate using a CoA-transferase such as the gene product of Ck-cat2. The 4-hydroxybutyrate can be produced by converting succinate semialdehyde using a 4-hydroxybutyrate dehydrogenase classified under EC 1.1.1.61. The succinate semialdehyde can be produced by converting succinyl-CoA using a succinate-semialdehyde dehydrogenase classified under EC 1.2.1.76.

The 2-butanol can be produced by converting butanone using a (R)-specific secondary alcohol dehydrogenase classified under EC 1.1.1.B4. The butanone can be produced by converting 2,3 butanediol using a propanediol dehydratase classified under EC 4.2.1.28. The 2,3 butanediol can be produced by converting (R)-acetoin using a (R,R)-butanediol dehydrogenase classified under EC 1.1.1.4. (R)-acetoin can be produced by converting 2-acetolactate using an acetolactate decarboxylase classified under EC 4.1.1.5. The 2-acetolactate can be produced by converting pyruvate using an acetolactate synthase classified under EC 2.2.1.6. The (R)

3-hydroxypent-4-enoate can be produced by converting 3-hydroxypent-4-enoyl-CoA using a thioesterase classified under EC 3.1.2.-. The 3-hydroxypent-4-enoyl-CoA can be produced by converting 2,4-pentadienoyl-CoA using an enoyl-CoA dehydratase 2 classified under EC 4.2.1. The 2,4-pentadienoyl-CoA can be produced by converting 2-hydroxypent-4-enoyl-CoA using a 2-Hydroxyisocaproyl-CoA dehydratase such as the gene products of the initiator HadI and HadBC. The 2-hydroxypent-4-enoyl-CoA can be produced by converting 2-hydroxypent-4-enoate using a CoA-transferase such the gene product of GctAB. The 2-hydroxypent-4-enoate can be produced by converting 2-oxopent-4-enoate using a (R)-2-hydroxyisocaproate dehydrogenase such as the gene product of LdhA from *Clostridium difficile*.

The (R)-hydroxypent-4-enoate can be produced by converting (R) 3-hydroxypent-4-enoyl-CoA using a thioesterase classified under EC 3.1.2.-. The (R) 3-hydroxypent-4-enoyl-CoA can be produced by converting 3-oxopent-4-enoyl-CoA using an acetoacetyl-CoA reductase classified under EC 1.1.1.36. The 3-oxopent-4-enoyl-CoA can be produced by converting propenoyl-CoA using a β-ketothiolase classified under EC 2.3.1.16. The (R)-hydroxypent-4-enoate can be produced by converting (R) 3-hydroxypent-4-enoyl-CoA using a thioesterase classified under EC 3.1.2.-. The (R) 3-hydroxypent-4-enoyl-CoA can be produced by converting (R)-3-hydroxypen-4-enoyl-[acp] using a (R)-3-hydroxyacyl-ACP:CoA transacylase such as the gene product of phaG. (R)-3-hydroxypen-4-enoyl-[acp] can be produced by converting 2,4 pentadienoyl-[acp] using a 3-hydroxyacyl-[acyl-carrier-protein] dehydratase classified under EC 4.2.1.59. (R) 3-hydroxypent-4-enoyl-CoA can be produced by converting 2,4-pentadienoyl-CoA using an enoyl-CoA dehydratase 2 classified under EC 4.2.1.119.

2-buten-1-ol diphosphate can be produced by converting 2-buten-1-ol phosphate using a phosphomevalonate kinase classified under EC 2.7.4.2 or using a diphosphokinase classified under EC 2.7.6.-. The 2-buten-1-ol phosphate can be produced by converting 2-buten-1-ol using a mevalonate kinase classified under EC 2.7.1.36. The 2-buten-1-ol can be produced by converting 2-buten-1-al using an allyl-alcohol dehydrogenase classified under EC 1.1.1.54. The 2-buten-1-al can be produced by converting crotonic acid using a long-chain-aldehyde dehydrogenase classified under EC 1.2.1.48. Crotonic acid can be produced by converting crotonyl-CoA using a succinate-CoA ligase classified under EC 6.2.1.5.

The 2-buten-1-ol diphosphate can be produced by converting 2-buten-1-ol using a diphosphokinase classified under EC 2.7.6.- such as a thiamine diphosphokinase classified under EC 2.7.6.2.

The 3-buten-2-ol diphosphate can be produced by converting 3-buten-2-ol using a diphosphokinase classified under EC 2.7.6.- or 3-buten-2-ol phosphate using a phosphomevalonate kinase classified under EC 2.7.4.2. The 3-buten-2-ol phosphate can be produced by converting 3-buten-2-ol using mevalonate kinase classified under EC 2.7.1.36.

In any of the methods described herein, the method can be performed using isolated enzymes, using cell lysates comprising the enzymes, or using a recombinant host. The recombinant host can be anaerobically, micro-aerobically or aerobically cultivated. Recombinant host cells can be retained in ceramic hollow fiber membranes to maintain a high cell density during fermentation. The principal carbon source fed to the fermentation can derive from biological or non-biological feedstocks. For example, the biological feedstock is or derives from monosaccharides, disaccharides, lignocellulose, hemicellulose, cellulose, lignin such as levulinic acid and furfural, lignin, triglycerides such as glycerol and fatty acids, agricultural waste or municipal waste. The non-biological feedstock is or derives from either natural gas, syngas, $CO_2/H_2$, methanol, ethanol, non-volatile residue (NVR) or caustic wash waste stream from cyclohexane oxidation processes.

The host microorganism can be a prokaryote from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lactobacillus delbrueckii*; or from the genus *Lactococcus* such as *Lactococcus lactis*. The host microorganism can be a eukaryote from the genus *Aspergillus* such as *Aspergillus niger*; from the genus *Saccharomyces* such as *Saccharomyces cerevisiae*; from the genus *Pichia* such as *Pichia pastoris*; from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*.

In the recombinant hosts described herein, the enzymes catalyzing the hydrolysis of propionyl-CoA and acetyl-CoA can be attenuated; the enzymes consuming propanoyl-CoA via the methyl-citrate cycle can be attenuated; the enzymes consuming propanoyl-CoA to pyruvate can be attenuated; the enzymes consuming propanoyl-CoA to malonyl-CoA can be attenuated; a feedback-resistant threonine deaminase can be genetically engineered into the host organism; the β-ketothiolases catalyzing the condensation of acetyl-CoA to acetoacetyl-CoA such as the gene products of AtoB or phaA can be attenuated; the polymer synthase enzymes in a host strain that naturally accumulates polyhydroxyalkanoates can be attenuated; a gene encoding a phosphotransacetylase, such as pta, can be attenuated; a gene encoding an acetate kinase degrading propanoate, such as ack, is attenuated; a gene encoding the degradation of pyruvate to lactate can be attenuated; a gene encoding the degradation of phophoenolpyruvate to succinate such as frdBC is attenuated; a gene encoding the degradation of acetyl-CoA to ethanol such as adhE can be attenuated; the enzymes catalyzing anaplerotic reactions supplementing the citric acid cycle intermediates can be amplified; a puridine nucleotide transhydrogenase gene such as UdhA can be overexpressed; a glyceraldehyde-3P-dehydrogenase gene such as GapN can be overexpressed in the host organisms; a malic enzyme gene such as maeA or maeB is overexpressed in the host organism; a glucose-6-phosphate dehydrogenase gene such as zwf is overexpressed in the host organism; a fructose 1,6 diphosphatase gene such as fbp is overexpressed in the host organism; the efflux of butadiene across the cell membrane to the extracellular media can be enhanced or amplified by genetically engineering structural modifications to the cell membrane; or the efflux of butadiene across the cell membrane to the extracellular media is enhanced or amplified by genetically engineering an increase to any associated transporter activity for butadiene; oxygenases degrading butadiene to toxic intermediates such as 1,2-epoxy-3-butene and 1,2:3,4-diepoxybutane are attenuated in the host organism.

In any of the methods described herein, the thioesterase can be the gene product of tesB; the acetoacetyl-CoA reductase can be the gene product of phaB; the acetyl-CoA C-acyltransferase can be the gene product of BktB; the enoyl-CoA hydratase can be the gene product of phaJ; the desaturase can be the gene product of MdpJ; the cytochrome P450 can be a gene product of the CYP4 family; the beta-ketoacyl-[acp] synthase I can be the gene product of tcsB; the acyl-transferase can be the gene product of tcsA.

Also provided by the document is a method of converting a butenol into butadiene. The method includes contacting 3-buten-2-ol with a linalool dehydratase, such that 1,3-butadiene is produced. The linalool dehydratase can be that classified under EC 4.2.1.127.

The details of one or more embodiments of the invention are set forth in the accompanying drawings and the description below. Other features, objects, and advantages of the invention will be apparent from the description and drawings, and from the claims. The word "comprising" in the claims may be replaced by "consisting essentially of" or with "consisting of," according to standard practice in patent law.

DESCRIPTION OF DRAWINGS

FIG. 13 is the amino acid sequences for MDD enzymes from *Saccharomyces cerevisiae* (Uniprot Accession No. P32377, SEQ ID NO:1), *Staphyloccocus epidermidis* (Uniprot Accession No. Q7CCL9, SEQ ID NO:2), and *Streptococcus pneumonia* (Uniprot Accession No. B8ZLF3, SEQ ID NO:3), highlighting the conserved residues within the catalytic cleft of the enzyme in bold.

DETAILED DESCRIPTION

In particular, this document provides enzymes, non-natural pathways, cultivation strategies, feedstocks, host microorganisms and attenuations to the host's biochemical network, which generates two terminal vinyl groups in four and five carbon chain metabolites leading to the synthesis of 1,3 butadiene (referred to as "butadiene" herein) from central precursors or central metabolites. As used herein, the term "central precursor" is used to denote a key metabolite in a pathway leading to the synthesis of butadiene. The term "central metabolite" is used herein to denote a metabolite that is produced in all microorganisms to support growth.

As such, host microorganisms described herein can include endogenous pathways that can be manipulated such that butadiene can be produced. In an endogenous pathway, the host microorganism naturally expresses all of the enzymes catalyzing the reactions within the pathway. A host microorganism containing an engineered pathway does not naturally express all of the enzymes catalyzing the reactions within the pathway but has been engineered such that all of the enzymes within the pathway are expressed in the host. Within an engineered pathway, the enzymes can be from a single source, i.e., from one species, or can be from multiple sources, i.e., different species. Nucleic acids encoding the enzymes described herein have been identified from various organisms and are readily available in publicly available databases such as GenBank or EMBL. Engineered hosts can naturally express none or some (e.g., one or more, two or more, three or more, four or more, five or more, or six or more) of the enzymes of the pathways described herein. Endogenous genes of the engineered hosts also can be disrupted to prevent the formation of undesirable metabolites or prevent the loss of intermediates in the pathway through other enzymes acting on such intermediates. Engineered hosts can be referred to as recombinant hosts or recombinant host cells. Thus, as described herein recombinant hosts can include nucleic acids encoding one or more of a decarboxylase, a dehydrogenase, a desaturase, a monooxygenase, an acyl [acyl carrier protein (acp)] dehydrogenase, a dehydratase, or a hydratase as described in more detail below.

In addition, the production of butadiene can be performed in vitro using the isolated enzymes described herein, using a lysate (e.g., a cell lysate) from a host microorganism as a source of the enzymes, or using a plurality of lysates from different host microorganisms as the source of the enzymes.

Figure 1:
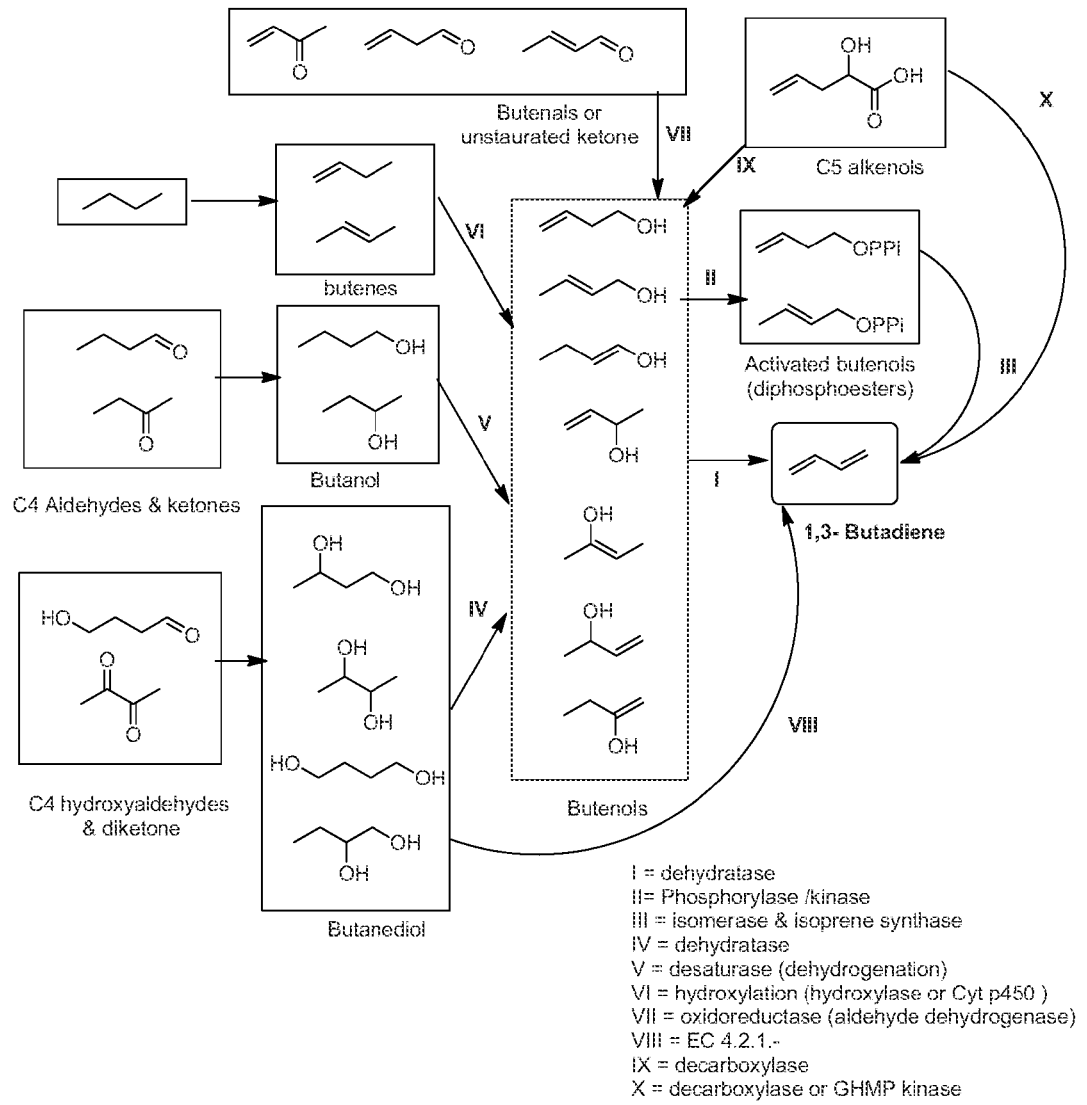
FIG. 1 is a schematic overview of the principal enzyme activities leading to 1,3 butadiene from C4 aldehydes and ketones, C4 hydroxy-aldehydes and diketones, butenes, butenals or unsaturated ketones, butenols, butanediols, C5 alkenols, and activated butenols.
Figure 2:
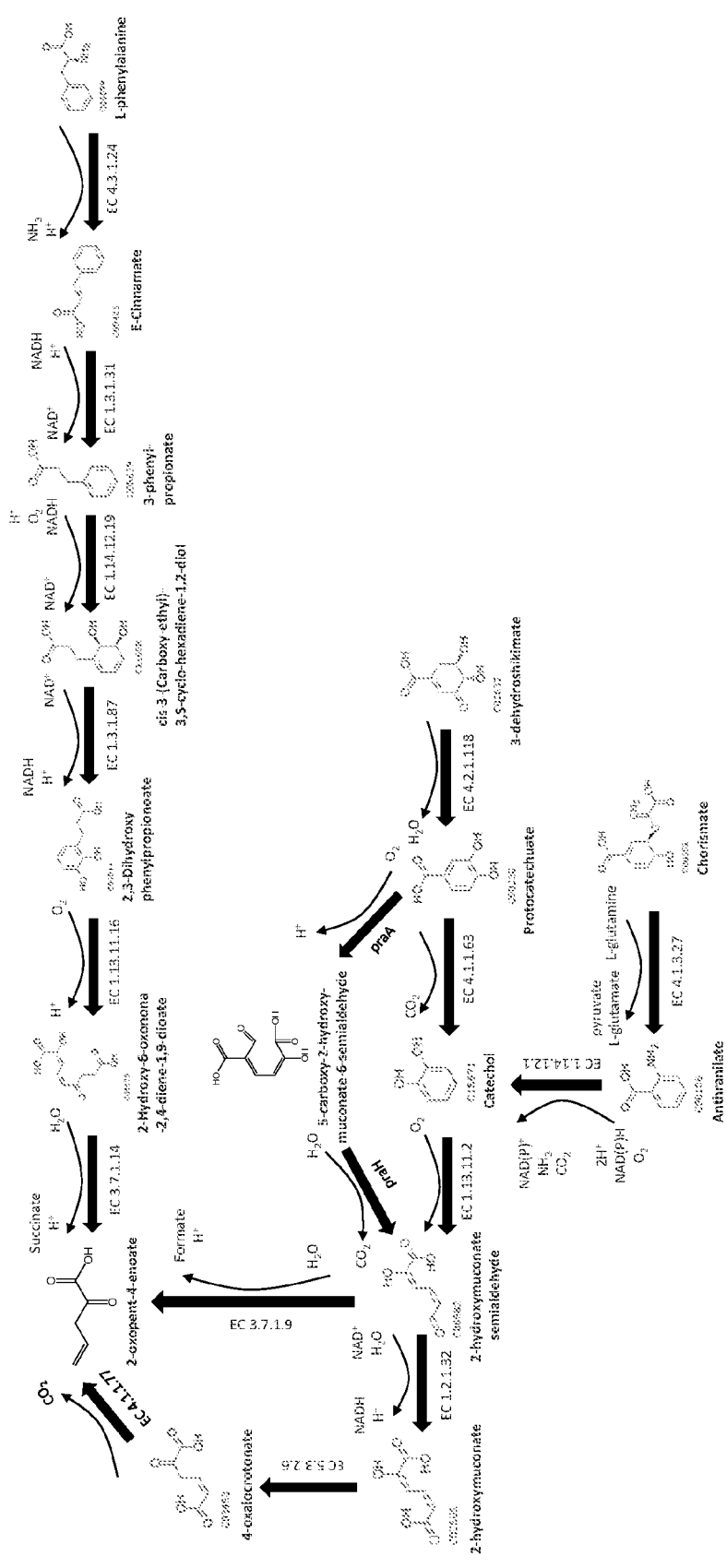
FIG. 2 is a schematic of biochemical pathways leading to butadiene using 2-oxopent-4-enoate as a central precursor.

FIG. 1 provides an overview of the principal enzyme activities that can be used to produce butadiene from various four or five carbon molecules, including C4 aldehydes and ketones, C4 hydroxy-aldehydes and diketones, butenes, butenals or unsaturated ketones, butenols, butanediols, C5 alkenols, and activated butenols.

4.1 Enzymes Generating the First Terminal Vinyl Group in the Biosynthesis of Butadiene As depicted in FIGS. 2-8, the first vinyl group can be formed in 4-oxalocrotonate, 2-hydroxymuconate semialdehyde, 2-hydroxy-6-oxonona-2,4-diene-1,9-dioate, propanoyl-CoA, lactoyl-CoA, 3-hydroxypropionyl-CoA, (R) 3-hydroxy-pentanoate, pent-2-enoyl-[acp], 5-hydroxypentanoyl-CoA (via 5-hydroxy-pent-2-enoyl-CoA), pent-3-enoyl-CoA 4-hydroxybutyryl-CoA, glutaconyl-CoA, (R) 3-hydroxybutanoyl-CoA or 2-butanol to produce such compounds as 2-oxopent-4-enoate, propenoyl-CoA, (R) 3-hydroxypent-4-enoate, (R) 3-hydroxypent-4-enoyl-[acp], 2,4-pentadienoyl-CoA, crotonyl-CoA, and 3-buten-2-ol.

In some embodiments, the first vinyl group leading to the synthesis of butadiene is enzymatically formed in 4-oxalocrotonate, 2-hydroxymuconate semialdehyde, or 2-hydroxy-6-oxonona-2,4-diene-1,9-dioate by 4-oxalocrotonate decarboxylase (EC 4.1.1.77), 2-hydroxymuconate-semialdehyde hydrolase (EC 3.7.1.9) or 2-hydroxy-6-oxonona-2,4-dienedioate hydrolase (EC 3.7.1.14) to produce 2-oxopent-4-enoate. See, e.g., FIG. 2.

In some embodiments, the first vinyl group leading to the synthesis of butadiene is enzymatically formed in propanoyl-CoA, lactoyl-CoA, 3-hydroxypropionyl-CoA by butyryl-CoA dehydrogenase (EC 1.3.8.1), medium-chain acyl-CoA dehydrogenase (EC 1.3.8.7), lactoyl-CoA dehydratase (EC 4.2.1.54) or 3-hydroxypropionyl-CoA dehydratase (EC 4.2.1.116) to produce propenoyl-CoA. See, e.g., FIG. 3.

In some embodiments, the first vinyl group leading to the synthesis of butadiene is enzymatically formed in (R) 3-hydroxy-pentanoate by a desaturase or monooxygenase such as the gene product of MdpJ or cytochrome P450 such as the gene product of the CYP4 family to produce (R) 3-hydroxy-pent-4-enoate. See, e.g., FIG. 4.

The gene product of the monooxygenase, MdpJ, desaturates the terminal of the ethyl group adjacent to a secondary alcohol (Schafer et al., *Applied and Environmental Microbiology*, 2012, 78(24)).

The gene product of the cytochrome P450 CYP4 family has displayed specificity for terminal desaturation rather than ω-hydroxylation of the C5 carboxylic acid, valproic acid (Rettie et al., *Biochemistry*, 1995, 34, 7889-7895).

In some embodiments, the first vinyl group leading to the synthesis of butadiene is enzymatically formed in pent-2-enoyl-[acp] by an acyl-[acp] dehydrogenase such as the gene product of TcsD to produce 2,4 pentadienoyl-[acp]. See, e.g., FIG. 5.

The gene product of the acyl-[acp] dehydrogenase TcsD desaturates the terminal methylene of pent-2-enoyl-[acp] to 2,4-pentadienoyl-[acp] (Mo et al., *J. Am. Chem. Soc.*, 2011, 133(4), 976-985).

In some embodiments, the first vinyl group leading to the synthesis of butadiene is enzymatically formed in 5-hydroxypentanoyl-CoA (via 5-hydroxy-pent-2-enoyl-CoA by a 5-hydroxyvaleryl-CoA dehydratase (EC 4.2.1.-) or 2,4-dienoyl coenzyme A reductase (EC 1.3.1.34) to produce 2,4-pentadienoyl-CoA. See, e.g., FIG. 6.

The dehydration of 5-hydroxyvalerate by 5-hydroxyvaleryl-CoA dehydratase to 2,4 pentadienoyl-CoA has been characterized from *Clostridium viride* (Eikmanns and Buckel, *Eur. J. Biochem.*, 1991, 197, 661-668).

In some embodiments, the first vinyl group leading to the synthesis of butadiene is enzymatically formed in 3-hydroxybutanoyl-CoA, 4-hydroxybutyryl-CoA or glutaconyl-CoA by an enoyl-CoA hydratase an by an enoyl-CoA hydratase (EC 4.2.1.119) such as the gene product of phaJ, a 4-hydroxybutanoyl-CoA dehydratase (EC 4.2.1.120) or a glutaconyl-CoA decarboxylase (EC 4.1.1.70) to produce crotonyl-CoA. See, e.g., FIG. 7.

The reversible dehydratase, 4-hydroxybutanoyl-CoA dehydratase, has been characterised has been characterized in several *Clostridium* species, such as *Clostridium kluyveri*, providing for a route to crotonyl-CoA via the central metabolite, succinate (Scherf et al., *Arch. Microbiol*, 1994, 161(3), 239-245; Sherf and Buckel, *Eur. J. Biochem.*, 1993, 215, 421-429).

The biotin-dependent decarboxylase, glutaconyl-CoA decarboxylase, maintains the position of the substrate's vinyl group after decarboxylation, providing a route to crotonyl-CoA via the central metabolite, 2-oxoglutarate (Kerstin et al., *The EMBO Journal*, 2003, 22(14), 3493-3502).

In some embodiments, the first vinyl group leading to the synthesis of butadiene is formed in 2-butanol by a desaturase or a monooxygenase such as the gene product of MdpJ or cytochrome P450 such as the gene product of the CYP4 family to produce 3-buten-2-ol. See, e.g., FIG. 8.

Figure 9:
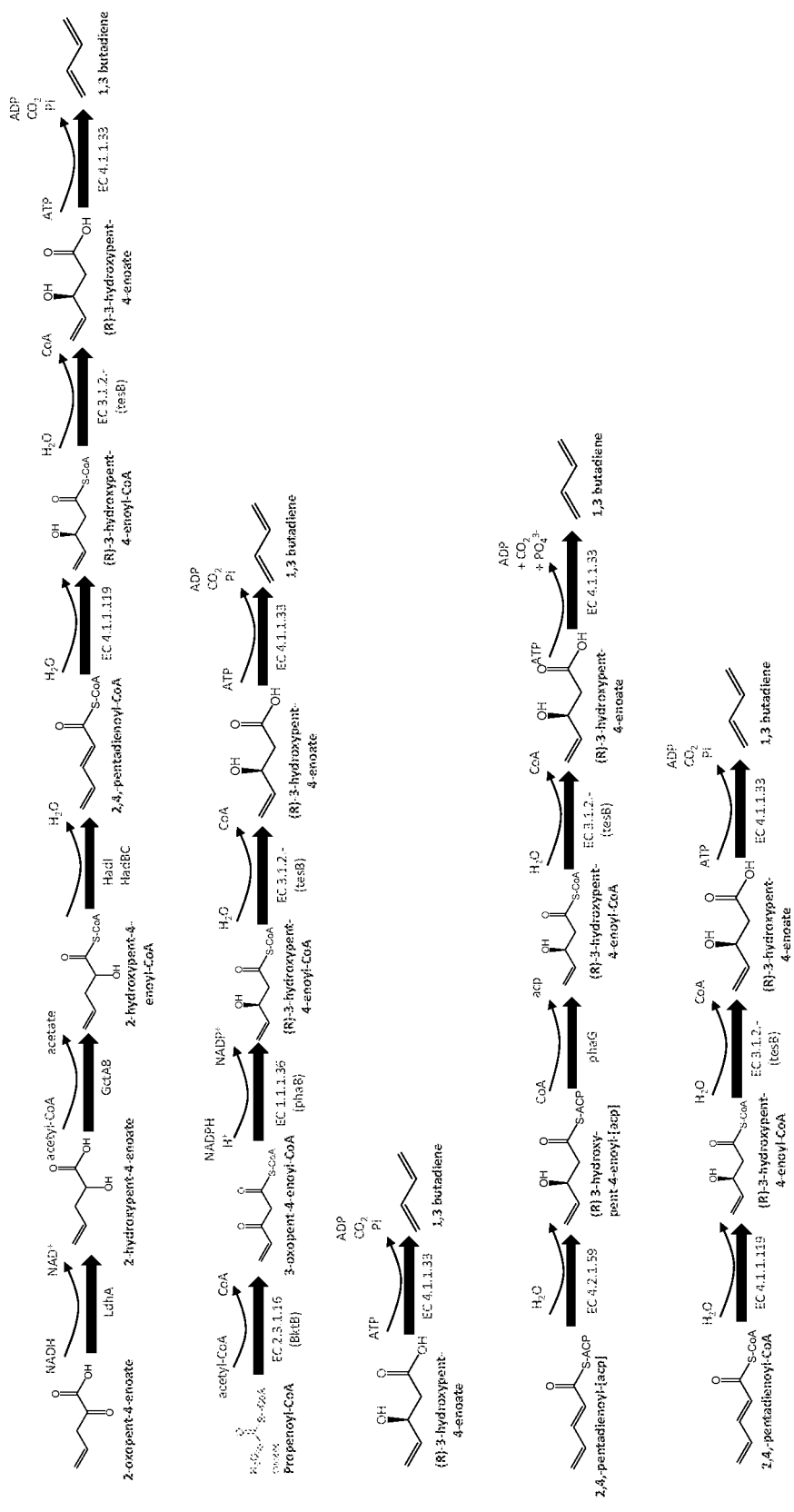
FIG. 9 is a schematic of biochemical pathways to synthesize butadiene using mevalonate diphosphate decarboxylase.
Figure 10:
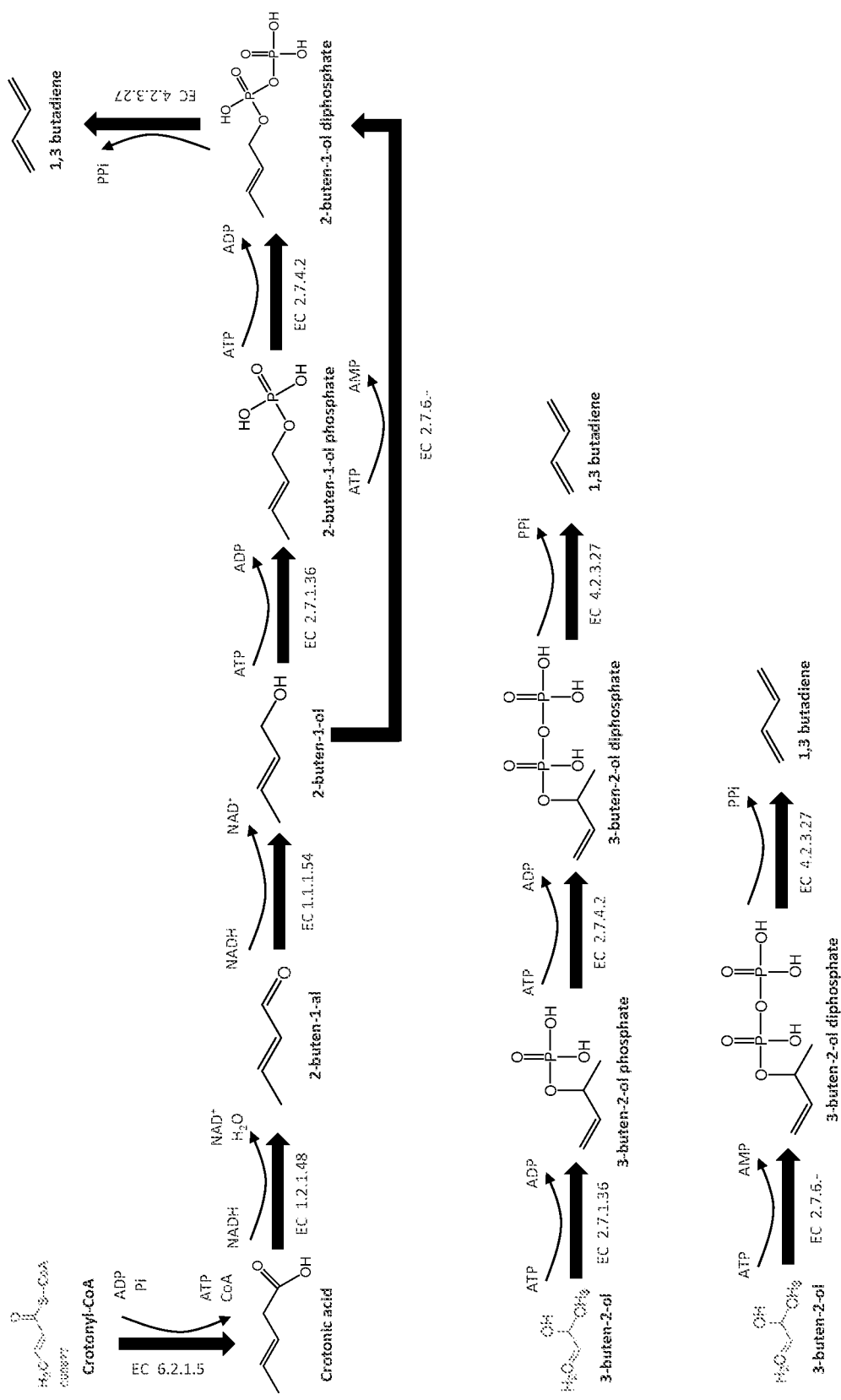
FIG. 10 is a schematic of biochemical pathways to synthesize butadiene using isoprene synthase.
Figure 11:
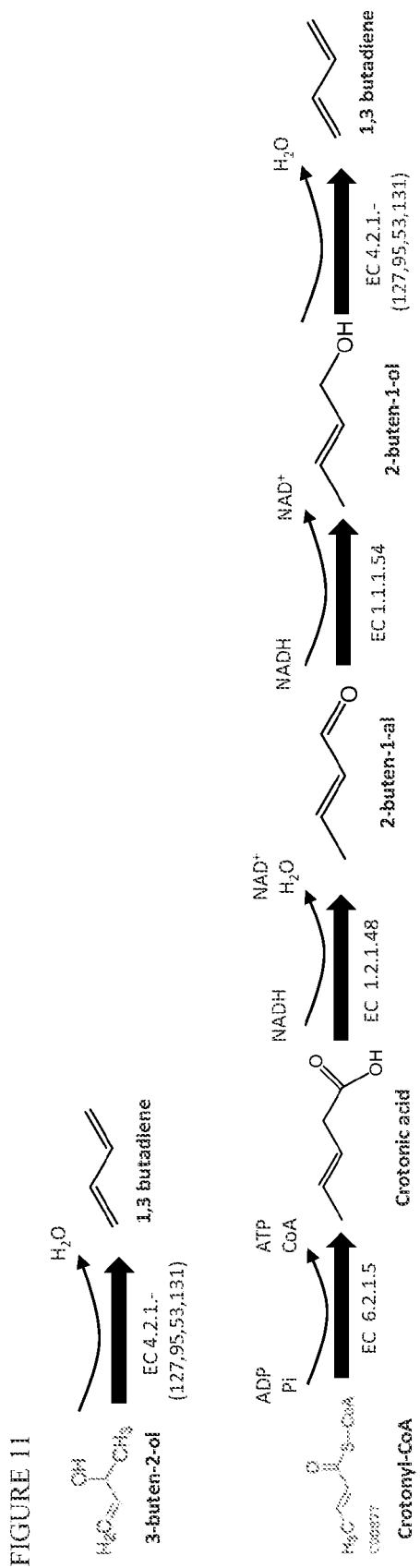
FIG. 11 is a schematic of biochemical pathways to synthesize butadiene using dehydratases.
Figure 12:
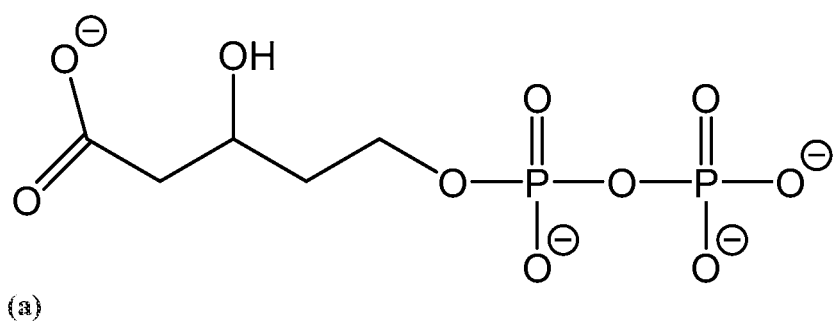
FIG. 12 is the structure of alternate substrates accepted by MDD, (a) is 3-hydroxy-5-diphosphatepentanoic acid and (b) is 3-hydroxy-3-methyl-butyrate.
Figure 12:
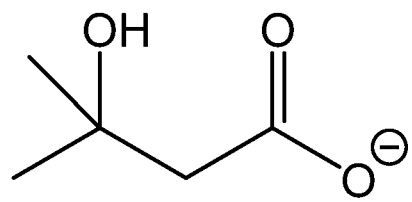

4.2 Enzymes Generating the Second Terminal Vinyl Group in the Biosynthesis of Butadiene As depicted in FIGS. 9-11, the second vinyl group can be enzymatically formed using a mevalonate diphosphate decarboxylase (MDD), an isoprene synthase (ISPS), or a dehydratase.

In some embodiments, the second vinyl group leading to the synthesis of butadiene is formed by a mevalonate diphosphate decarboxylase (MDD), an enzyme classified under EC 4.1.1.33. See, e.g., FIG. 9.

In some embodiments, the second vinyl group leading to the synthesis of butadiene is enzymatically formed by an isoprene synthase (ISPS), an enzyme classified under 4.2.3.27. See, e.g., FIG. 10.

In some embodiments, the second vinyl group leading to the synthesis of butadiene is enzymatically formed by a dehydratase in enzyme class EC 4.2.1.-, particularly linalool dehydratase (EC 4.2.1.127), kievitone hydratase (EC 4.2.1.95), oleate hydratase (EC 4.2.1.53) or carotenoid 1,2-hydratase (EC 4.2.1.131). See, e.g., FIG. 11.

Linalool may be regarded as 3-buten-2-ol substituted with an isohexenyl R-group at the alpha position. The dehydration of linalool to myrcene is favored thermodynamically and likely proceeds via deprotonation, where the R-group has no mechanistic role (Bordkorb et al., *J. Biol. Chem.*, 2010, 285(40), 30436-30442).

Oleate hydratase converts long chain unsaturated fatty acid, oleic acid, to (R)-10-hydroxystearate. However, in screening 165 homologues to the oleate hydratase sequence of *E. meningoseptica*, several accepted isobutanol as substrate forming isobutene (Bianca et al., *Appl. Microbiol. Biotechnol.*, 2012, 93, 1377-1387).

4.3 Biochemical Pathways 4.3.1 Pathways Using 2-oxopent-4-enoate as Central Precursor to Butadiene Pathways leading to the production of 2-oxopent-4-enoate from aromatic compounds such as protocatechuate (Kasai et al., *J. Bacteriol.*, 2009, 191(21), 6758-6768), catechol (He and Spain, *J. Bacteriol.*, 1998, 180(9), 2502-2506), anthranilate (Muraki et al., *Applied and Environmental Microbiology*, 2003, 69(3), 1564-1572) and 3-phenylpropionic acid (Ferrandez et al., *J. Bacteriol.*, 1997, 179(8), 2573-2581) are well characterized. Carbon flux from the central metabolites may be directed to these degradation pathways via 3-dehydroshikimate by 3-dehydroshikimate dehydratase (EC 4.2.1.118), via chorismate by anthranilate synthase (EC 4.1.3.27), and via L-phenylalanine by phenylalanine ammonia lyase (EC 4.3.1.24) and 2-enoate reductase (EC 1.3.1.31).

In some embodiments, 2-oxopent-4-enoate is synthesized from the central metabolite, chorismate, by conversion to anthranilate by anthranilate synthase (EC 4.1.3.27); followed by conversion to catechol by anthranilate 1,2-dioxygenase (EC 1.14.12.1); followed by conversion to 2-hydroxymuconate semialdehyde by catechol 2,3-dioxygenase (EC 1.13.11.2); followed by conversion to 2-oxopent-4-enoate by 2-hydroxymuconate-semialdehyde hydrolase (EC 3.7.1.9). In addition, 2-hydroxymuconate semialdehyde can be converted to 2-hydroxymuconate by aminomuconate semialdehyde dehydrogenase (EC 1.2.1.32), 2-hydroxymuconate can be converted to 4-oxalocrotonate by 2-hydroxymuconate tautomerase (EC 5.3.2.6), and 4-oxalocrotonate can be converted to 2-oxopent-4-enoate 4-oxalocrotonate decarboxylase (EC 4.1.1.77). See, e.g., FIG. 2.

In some embodiments, 2-oxopent-4-enoate is synthesized from the central metabolite, 3-dehydroshikimate, by conversion to protocatechuate by 3-dehydroshikimate dehydratase (EC 4.2.1.118); followed by conversion to catechol by protocatechuate decarboxylase (EC 4.1.1.63); followed by conversion to 2-hydroxymuconate semialdehyde by catechol 2,3-dioxygenase (EC 1.13.11.2); followed by conversion to 2-oxopent-4-enoate by 2-hydroxymuconate-semialdehyde hydrolase (EC 3.7.1.9) or by aminomuconate semialdehyde dehydrogenase (EC 1.2.1.32), 2-hydroxymuconate tautomerase (EC 5.3.2.6) and 4-oxalocrotonate decarboxylase (EC 4.1.1.77). See, e.g., FIG. 2.

In some embodiments, 2-oxopent-4-enoate is synthesized from the central metabolite, 3-dehydroshikimate, by conversion to protocatechuate by 3-dehydroshikimate dehydratase (EC 4.2.1.118); followed by conversion to 5-carboxy-2-hydroxymuconate-6-semialdehyde by protocatechuate 2,3-dioxygenase such as the gene product of praA; followed by conversion to 2-hydroxymuconate semialdehyde by 5-carboxy-2-hydroxymuconate-6-semialdehyde decarboxylase such as the gene product of praH; followed by conversion to 2-oxopent-4-enoate by 2-hydroxymuconate-semialdehyde hydrolase (EC 3.7.1.9) or by aminomuconate semialdehyde dehydrogenase (EC 1.2.1.32), 2-hydroxymuconate tautomerase (EC 5.3.2.6) and 4-oxalocrotonate decarboxylase (EC 4.1.1.77). See, e.g., FIG. 2.

In some embodiment, 2-oxopent-4-enoate is synthesized from the central metabolite, L-phenylalanine, by conversion to E-cinnamate by phenylalanine ammonia-lyase (EC 4.3.1.24); followed by conversion to 3-phenyl-propionate by 2-enoate reductase (EC 1.3.1.31); followed by conversion to cis-3-(carboxy-ethyl)-3,5-cyclo-hexadiene-1,2-diol by 3-phenylpropanoate dioxygenase (EC 1.14.12.19); followed by conversion to 2,3-dihydroxyphenylpropionate by 3-(cis-5,6-dihydroxycyclohexa-1,3-dien-1-Apropanoate dehydrogenase (EC 1.3.1.87); followed by conversion to 2-hydroxy-6-oxonona-2,4-diene-1,9-dioate by 3-carboxyethylcatechol 2,3-dioxygenase (EC 1.13.11.16); followed by conversion to 2-oxopent-4-enoate by 2-hydroxy-6-oxonona-2,4-dienedioate hydrolase (EC 3.7.1.14). See, e.g., FIG. 2.

In some embodiments, butadiene is synthesized from 2-oxopent-4-enoate by conversion to 2-hydroxypent-4-enoate by (R)-2-hydroxyisocaproate dehydrogenase such as the gene product of LdhA; followed by conversion to 2-hydroxypent-4-enoyl-CoA by CoA transferase such as the gene product of GctAB; followed by conversion to 2,4-pentadienoyl-CoA by 2-Hydroxyisocaproyl-CoA dehydratase such as the gene products of the initiator HadI and HadBC; followed by conversion to (R)-3-hydroxypent-4-enoyl-CoA by enoyl-CoA dehydratase 2 (EC 4.1.1.119); followed by conversion to (R)-3-hydroxypent-4-enoate by a thioesterase (EC 3.1.2.-) such as the gene product of tesB; followed by conversion to butadiene by mevalonate diphosphate decarboxylase (EC 4.1.1.33). See, e.g., FIG. 9.

(R)-2-hydroxyisocaproate dehydrogenase (gene product of LdhA) accepts 2-oxopentanoate and 2-oxohexanoate as substrates (Kim, On the enzymatic mechanism of 2-hydroxyisocaproyl-CoA dehydratase from *Clostridium difficile*, 2004, Ph.D. dissertation, Philipps-Universitat, Marburg, 2004). 2-oxopentanoate is a near substrate analogue of 2-oxopent-4-enoate.

Glutaconate CoA-transferase (GctAB) is a promiscuous enzyme accepting carbon chains ranging from 3 to 6 carbons in length, that are branched and unbranched, alpha-substituted and unsubstituted monocarboxylic and dicarboxylic acids (see, e.g., Buckel et al., *Eur. J. Biochem.*, 1981, 118, 315-321). 2-hydroxypent-4-enoic acid has comparable structure and functional groups where CoA activation is required for the activity of 2-Hydroxyisocaproyl-CoA dehydratase.

2-Hydroxyisocaproyl-CoA dehydratase (HadI & HadBC) accepts the substrate analogue 2-hydroxypent-4-enoyl-CoA as substrate, synthesizing 2,4-pentadienoyl-CoA (Kim et al., Nature Letters, 2008, 452, 239-243).

The hydrolysis of short and medium carbon chain acyl-CoA substrates has been demonstrated using the gene product of tesB (Liu et al., *Appl. Microbiol. Biotechnol.*, 2007, 76, 811-818). The thioesterase II gene product of tesB hydrolyses (R)-3-hydroxypentanoyl-CoA efficiently (Martin and Prather, *Journal of Biotechnology*, 2009, 139, 61-67).

Figure 3:
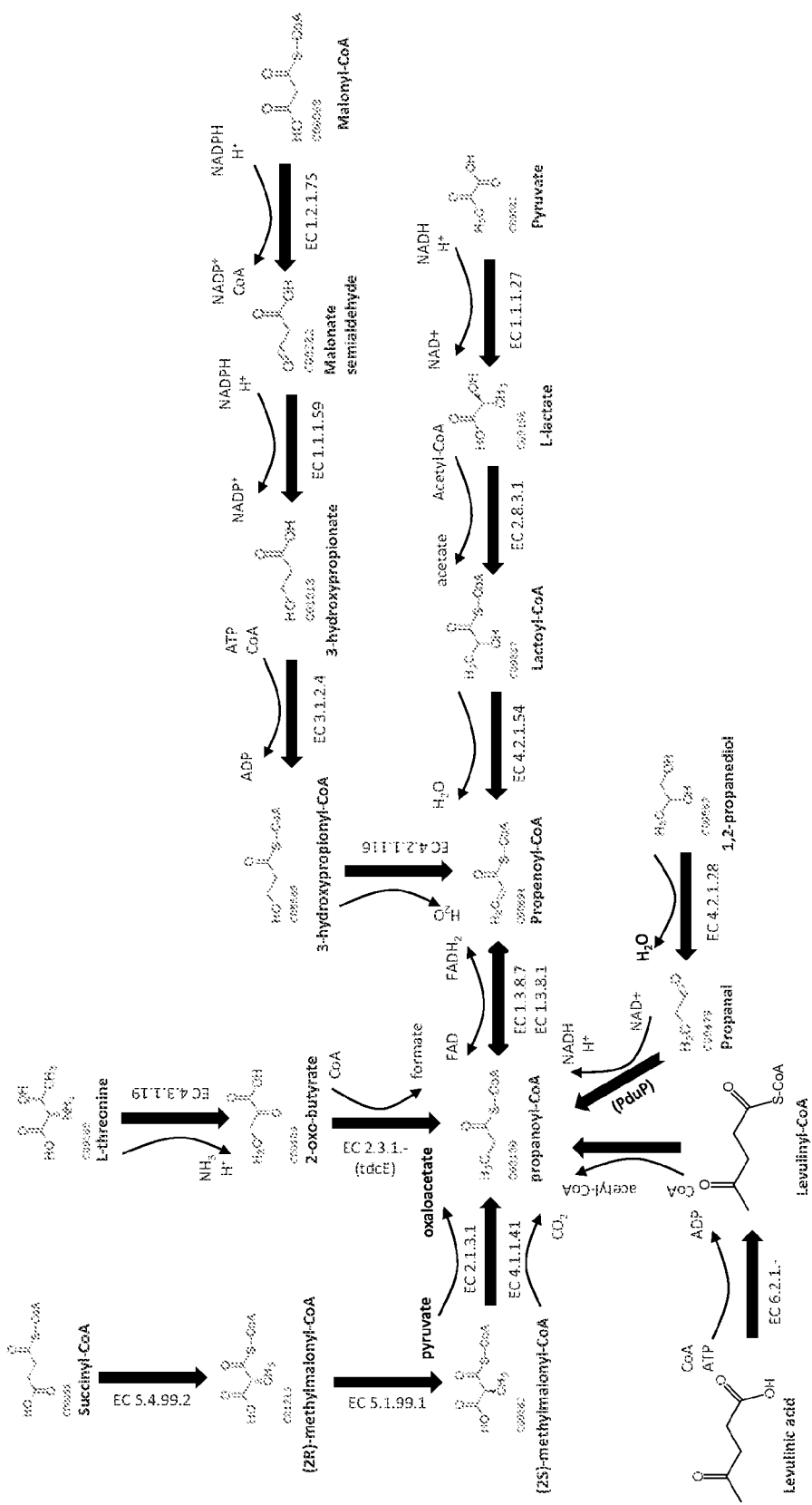
FIG. 3 is a schematic of biochemical pathways leading to butadiene using propenoyl-CoA as a central precursor.
Figure 4:
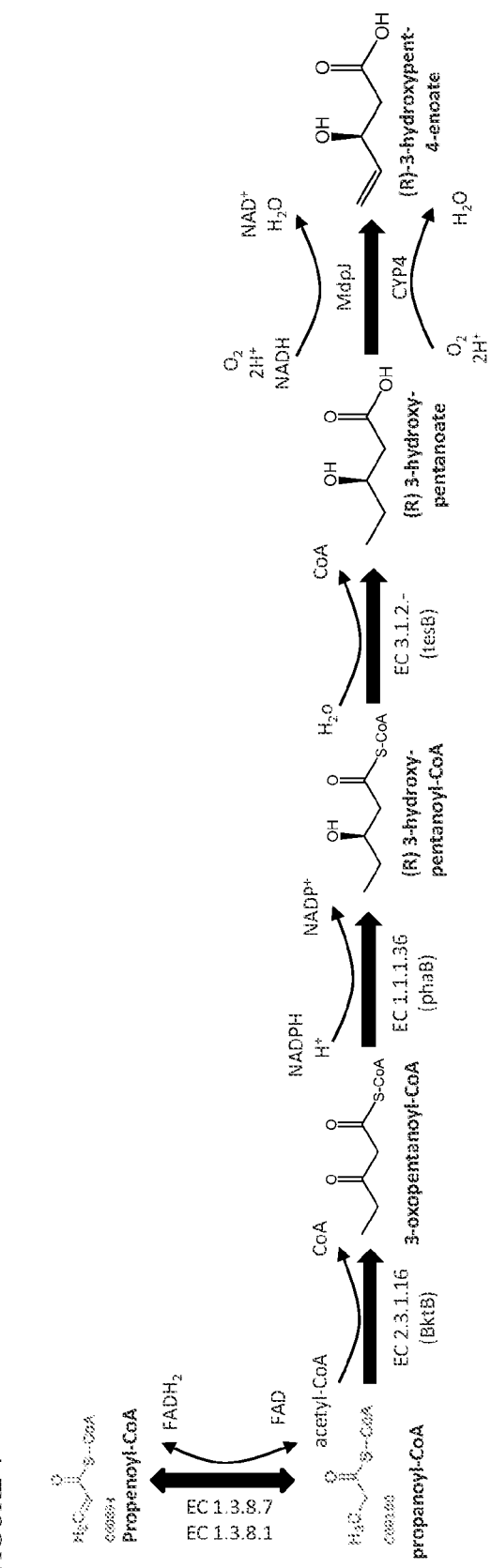
FIG. 4 is a schematic of biochemical pathways leading to butadiene using 3-hydroxy-4-pentenoate as a central precursor.
Figure 5:
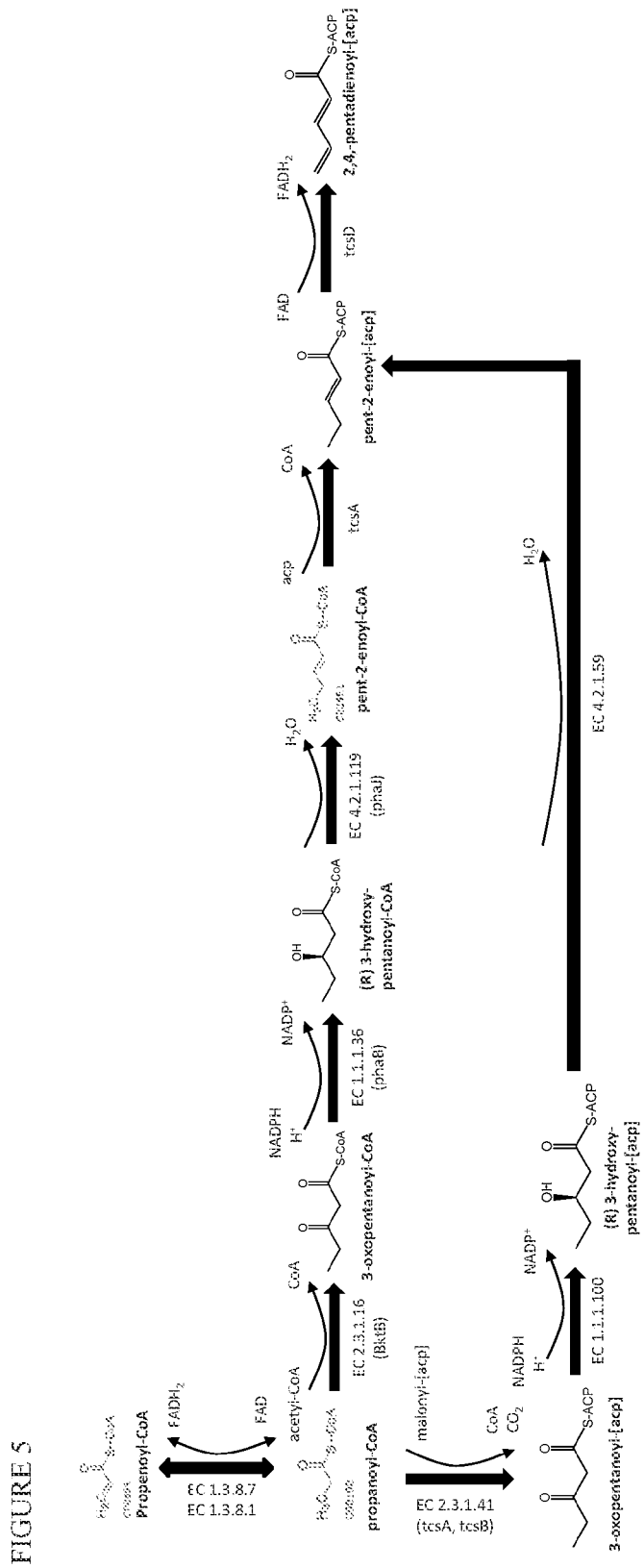
FIG. 5 is a schematic of biochemical pathways leading to butadiene using 2,4-pentadienoyl-[acp] as a central precursor.
Figure 6:
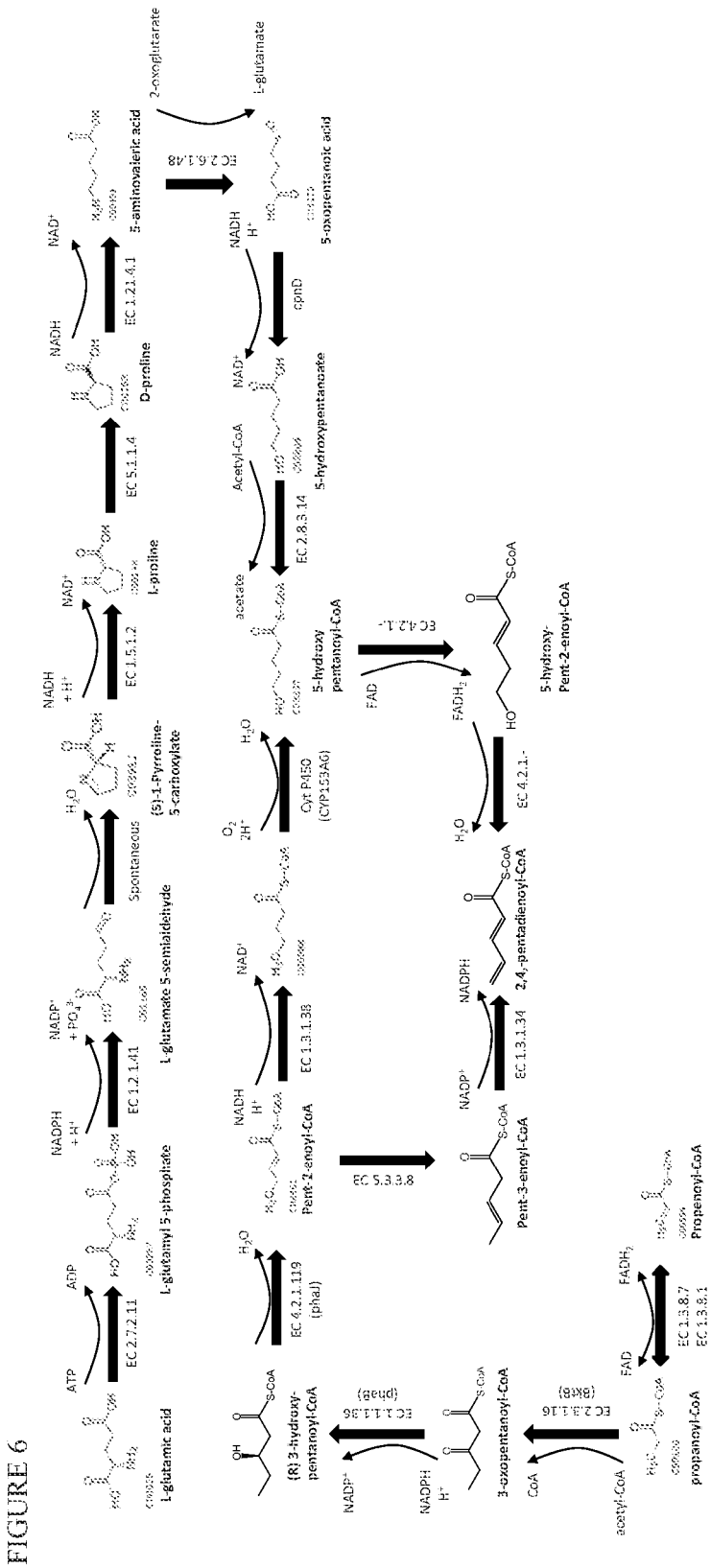
FIG. 6 is a schematic of biochemical pathways leading to butadiene using 2,4-pentadienoyl-CoA as a central precursor.
Figure 7:
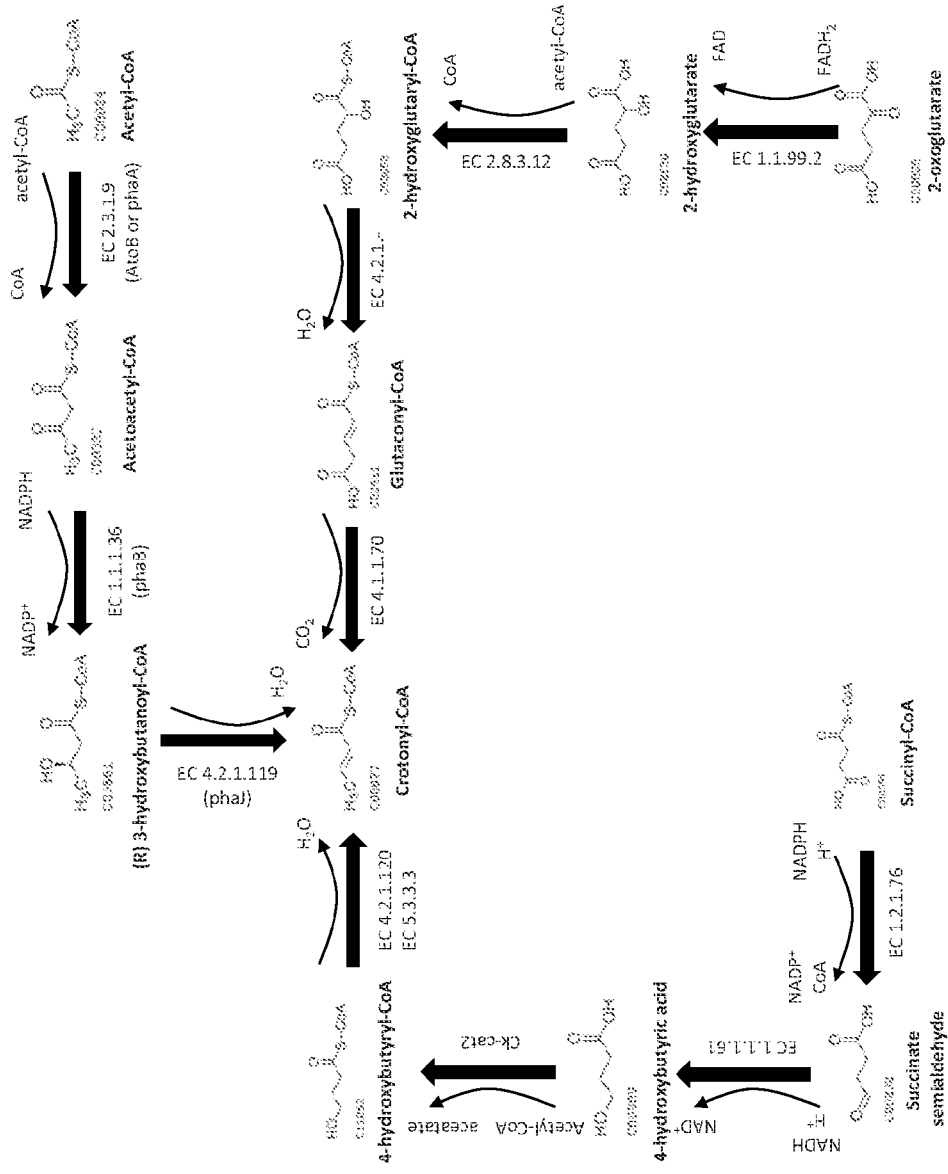
FIG. 7 is a schematic of biochemical pathways leading to butadiene using crotonyl-CoA as a central precursor.
Figure 8:
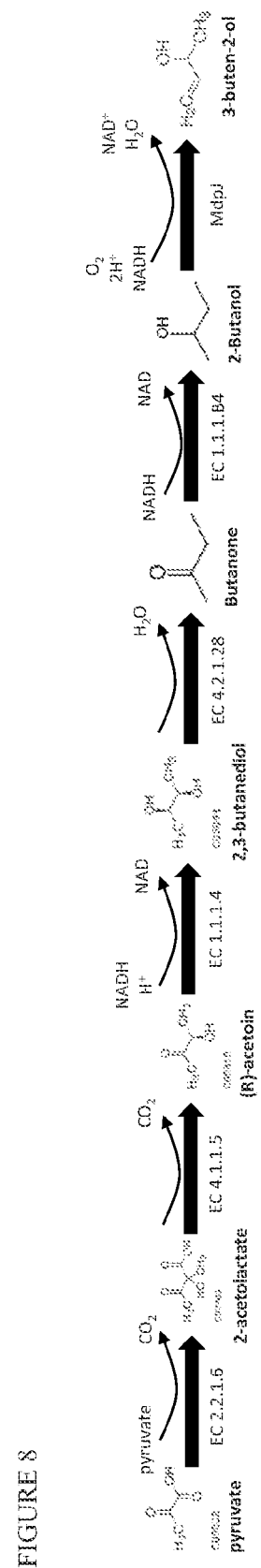
FIG. 8 is a schematic of biochemical pathways leading to butadiene using 3-buten-2-ol as a central precursor.

4.3.2 Pathways to Propanoyl-CoA as Precursor Leading to Central Precursors to Butadiene In some embodiments, propanoyl-Coenzyme A (CoA) is a precursor leading to central precursors in the synthesis of butadiene (see, e.g., FIG. 3).

In some embodiments, propanoyl-CoA is synthesized from the central metabolite, succinyl-CoA, by conversion of succinyl-CoA to (2R)-methylmalonyl-CoA by methylmalonyl-CoA mutase (EC 5.4.99.2); followed by conversion to (2S)-methylmalonyl-CoA by methylmalonyl-CoA epimerase (EC 5.1.99.1); followed by conversion to propanoyl-CoA by methylmalonyl-CoA carboxytransferase (EC 2.1.3.1) or methylmalonyl-CoA decarboxylase (EC 4.1.1.41). See e.g., FIG. 3.

In some embodiments, propanoyl-CoA is synthesized from the central metabolite, L-threonine, by conversion of L-threonine to 2-oxobutyrate by threonine ammonia lyase (EC 4.3.1.19); followed by conversion to propanoyl-CoA by 2-ketobutyrate formate-lyase such as the gene product of tdcE (EC 2.3.1.-) (see, Tseng et al., *Microbial Cell Factories*, 2010, 9:96). See, e.g., FIG. 3.

The intracellular accumulation of propanoyl-CoA from L-threonine as a precursor to other products has been demonstrated (Tseng et al., *Microbial Cell Factories*, 2010, 9:96).

In some embodiments, propanoyl-CoA is synthesized from 1,2-propanediol by conversion to propanal by propanediol dehydratase (EC 4.2.1.28); followed by conversion to propanoyl-CoA by CoA-dependent propionaldehyde dehydrogenase such as the gene product ofpduP (see Luo et al., *Bioresource Technology*, 2012, 103, 1-6) See, e.g., FIG. 3.

The intracellular accumulation of propanoyl-CoA from 1,2 propanediol has been reported (Luo et al., *Bioresource Technology*, 2012, 103, 1-6).

In some embodiments, propanoyl-CoA is synthesized from the carbon source, levulinic acid, by conversion of levulinic acid to levulinyl-CoA by acyl-CoA synthetase or ligase (EC 6.2.1.-); followed by conversion to propanoyl-CoA by a transferase in EC 2.3.1.- (Jaremko and Yu, *Journal of Biotechnology*, 2011, 155, 2011, 293-298). See, e.g., FIG. 3.

In some embodiments, propanoyl-CoA is synthesized from the central metabolite, pyruvate, by conversion of pyruvate to L-lactate by L-lactate dehydrogenase (EC 1.1.1.27); followed by conversion to lactoyl-CoA by proprionate CoA-transferase (EC 2.8.3.1); followed by conversion to propenoyl-CoA by lactoyl-CoA dehydratase (EC 4.2.1.54); followed by conversion to propanoyl-CoA by butyryl-CoA dehydrogenase (EC 1.3.8.1) or medium-chain acyl-CoA dehydrogenase (EC 1.3.8.7). See, e.g., FIG. 3.

In some embodiments, propanoyl-CoA is synthesized from the central metabolite, malonyl-CoA, by conversion of malonyl-CoA to malonate semialdehyde by malonyl-CoA reductase (EC 1.2.1.75); followed by conversion to 3-hydroxypropionate by 3-hydroxypropionate dehydrogenase (EC 1.1.1.59); followed by conversion to 3-hydroxypropionyl-CoA by 3-hydroxyisobutyryl-CoA hydrolase (EC 3.1.2.4); followed by conversion to propenoyl-CoA by 3-hydroxypropionyl-CoA dehydratase (EC 4.2.1.116); followed by conversion to propanoyl-CoA by butyryl-CoA dehydrogenase (EC 1.3.8.1) or medium-chain acyl-CoA dehydrogenase (EC 1.3.8.7). See, e.g., FIG. 3.

4.3.3 Pathways Using Propenoyl-CoA as Central Precursor to Butadiene

In some embodiments, propenoyl-CoA is synthesized from propanoyl-CoA by butyryl-CoA dehydrogenase (EC 1.3.8.1) or medium-chain acyl-CoA dehydrogenase (EC 1.3.8.7). See, e.g., FIG. 3.

In some embodiments, propenoyl-CoA is synthesized from the central metabolite, pyruvate, by conversion of pyruvate to L-lactate by L-lactate dehydrogenase (EC 1.1.1.27); followed by conversion to lactoyl-CoA by propionate CoA-transferase (EC 2.8.3.1); followed by conversion to propenoyl-CoA by lactoyl-CoA dehydratase (EC 4.2.1.54). See, e.g., FIG. 3.

In some embodiments, propenoyl-CoA is synthesized from the central metabolite, malonyl-CoA, by conversion to malonate semialdehyde by malonyl-CoA reductase (EC 1.2.1.75); followed by conversion to 3-hydroxypropionate by 3-hydroxypropionate dehydrogenase (EC 1.1.1.59); followed by conversion to 3-hydroxypropionyl-CoA by 3-hydroxyisobutyryl-CoA hydrolase (EC 3.1.2.4); followed by conversion to propenoyl-CoA by 3-hydroxypropionyl-CoA dehydratase (EC 4.2.1.116). See, e.g., FIG. 3.

In some embodiments, butadiene is synthesized from propenoyl-CoA by conversion to 3-oxopent-4-enoyl-CoA by β-ketothiolase such as EC 2.3.1.16; followed by conversion to (R)-3-hydroxypent-4-enoyl-CoA by acetoacetyl-CoA reductase (EC 1.1.1.36) such as the gene product of phaB; followed by conversion to (R)-3-hydroxypent-4-enoate by a thioesterase (EC. 3.1.2.-) such as the gene product of tesB; followed by conversion to butadiene by mevalonate diphosphate decarboxylase (EC 4.1.1.33). See, e.g., FIG. 9.

4.3.4 Pathway Using (R) 3-hydroxypent-4-enoate as Central Precursor to Butadiene In some embodiments, (R) 3-hydroxypent-4-enoate is synthesized from propanoyl-CoA by conversion to 3-oxopentanoyl-CoA by acetyl-CoA C-acyltransferase (EC 2.3.1.16); followed by conversion to (R) 3-hydroxypentanoyl-CoA by acetoacetyl-CoA reductase (EC 1.1.1.36) such as the gene product of phaB; followed by conversion to (R) 3-hydroxypent-4-enoyl-CoA by a thioesterase such as the gene product of tesB (EC 3.1.2.-); followed by conversion to (R) 3-hydroxypent-4-enoate by a desaturase such as the gene product of MdpJ or cytochrome P450 such as the gene product of the CYP4 family. See, e.g., FIG. 4.

Terminal desaturation of carboxylic acids by cytochrome P450 enzymes in the CYP4 family has been elucidated. CYP4B1 desaturates the twelve carbon chain length fatty acid lauric acid by removing the ω-1 hydrogen at the terminal (Guan et al., Chemico-Biology Interactions, 1998, 110, 103-121).

In some embodiments, butadiene is synthesized from (R) 3-hydroxypent-4-enoate by mevalonate diphosphate decarboxylase (EC 4.1.1.33). See, e.g., FIG. 9.

4.3.5 Pathway Using 2,4-pentadienoyl-[acp] as Central Precursor to Butadiene

In some embodiments, (R) 3-hydroxypent-4-enoyl-[acp] is synthesized from propanoyl-CoA by conversion of propanoyl-CoA to 3-oxopentanoyl-CoA by acetyl-CoA C-acyltransferase (EC 2.3.1.16); followed by conversion to (R) 3-hydroxypentanoyl-CoA by 3-hydroxyacyl-CoA dehydrogenase (EC 1.1.1.36) such as the gene product of phaB; followed by conversion to pent-2-enoyl-CoA by enoyl-CoA hydratase (EC 4.2.1.119) such as the gene product of phaJ; followed by conversion to pent-2-enoyl-[acp] in reaction with the gene product of an acyl transferase such as tcsA; followed by conversion to (R) 2,4-pentadienoyl-[acp] by an acyl-[acp] dehydrogenase such as the gene product of TcsD. See, e.g., FIG. 5.

In some embodiments, (R) 3-hydroxypent-4-enoyl-[acp] is synthesized from propanoyl-CoA by conversion of propanoyl-CoA to 3-oxopentanoyl-[acp] by a Beta-ketoacyl-[acp] synthase I (EC 2.3.1.41) such as tcsB and an acyltransferase such as tcsA; followed by conversion to (R) 3-hydroxypentanoyl-CoA by 3-oxoacyl-[acyl-carrier-protein] reductase (EC 1.1.1.100); followed by conversion to pent-2-enoyl-[acp] by 3-Hydroxyacyl-[acp] dehydratase (EC 4.2.1.59); followed by conversion to 2,4-pentadienoyl-[acp] by acyl-[acp] dehydrogenase such as the gene product of TcsD. See, e.g., FIG. 5.

In some embodiments, butadiene is synthesized from (R)-3-hydroxypent-4-enoyl-[acp] by conversion to (R)-3-hydroxypent-4-enoyl-CoA by (R)-3-hydroxyacyl-[acp]: CoA transacylase such as the gene product of phaG; followed by conversion to (R)-3-hydroxypent-4-enoate by a thioesterase such as the gene product of tesB; followed by conversion to butadiene by mevalonate diphosphate decarboxylase (EC 4.1.1.33). See, e.g., FIG. 9.

The gene product of phaJ (EC 4.2.1.119) is a key enzyme for providing short and medium chain R-specific 3-hydroxyacyl-CoA monomers from fatty acid synthesis to polyhydroxyalkanoate synthase enzymes (Chung and Rhee, Biosci. Biotechnol. Biochem., 2012, 76(3), 613-616; Tsuge et al., International Journal of Biological Macromolecules, 2003, 31, 195-205).

Utilizing 4-pentenoic acid as a carbon source to polyhydroxyalkanoate-producing bacteria produces (R)-3-hydroxypent-4-enoate via beta-oxidation. Accordingly, 4-pentenoic acid is converted to 2,4-pentadienoyl-CoA which is made available to polymer synthase enzymes after hydration to (R)-3-hydroxypent-4-enoate by R-specific enoyl-CoA dehydrase activity (Ulmer et al., Macromolecules, 1994, 27, 1675-1679).

4.3.6 Pathway Using 2,4 pentadienoyl-CoA as Central Precursor to Butadiene

In some embodiments, 2,4-pentadienoyl-CoA is synthesized from propanoyl-CoA by conversion of propanoyl-CoA to 3-oxo-pentanoyl-CoA by an acetyl-CoA C-acyltransferase (EC 2.3.1.16) such as the gene product of bktB; followed by conversion to (R) 3-hydroxypentanoyl-CoA by a 3-hydroxyacyl-CoA dehydrogenase (EC 1.1.1.36) such as the gene product of phaB; followed by conversion to pent-2-enoyl-CoA by an enoyl-CoA hydratase (EC 4.2.1.119) such as the gene product of phaJ; followed by conversion to pent-3-enoyl-CoA by an isomerase (EC 5.3.3.8); followed by conversion to 2,4-pentadienoyl-CoA by a 2,4-dienoyl coenzyme A reductase (EC 1.3.1.34). See, e.g., FIG. 6.

In some embodiments, 2,4-pentadienoyl-CoA is synthesized from propanoyl-CoA by conversion of propanoyl-CoA to 3-oxo-pentanoyl-CoA by an acetyl-CoA C-acyltransferase (EC 2.3.1.16) such as the gene product of bktB; followed by conversion to (R) 3-hydroxypentanoyl-CoA by a 3-hydroxyacyl-CoA dehydrogenase (EC 1.1.1.36) such as the gene product of phaB; followed by conversion to pent-2-enoyl-CoA by an enoyl-CoA hydratase (EC 4.2.1.119)

such as the gene product of phaJ; followed by conversion to pent-3-enoyl-CoA by an isomerase (EC 5.3.3.8); followed by conversion to 2,4-pentadienoyl-CoA by a 2,4-dienoyl coenzyme A reductase (EC 1.3.1.34). See, e.g., FIG. 6.

In some embodiments, 2,4-pentadienoyl-CoA is synthesized from propanoyl-CoA by conversion of propanoyl-CoA to 3-oxo-pentanoyl-CoA by an acetyl-CoA C-acyltransferase (EC 2.3.1.16) such as the gene product of bktB; followed by conversion to (R) 3-hydroxypentanoyl-CoA by a 3-hydroxyacyl-CoA dehydrogenase (EC 1.1.1.36) such as the gene product of phaB; followed by conversion to 2E-pentenoyl-CoA by an enoyl-CoA hydratase (EC 4.2.1.119) such as the gene product of phaJ; followed by conversion to pentanoyl-CoA by a trans-2-enoyl-CoA reductase such as EC 1.3.1.38; followed by conversion to 5-hydroxypentanoyl-CoA by a cytochrome P450 monooxygenase such as the gene product of CYP153A6; followed by conversion to 2,4-pentadienoyl-CoA by a 5-hydroxyvaleryl-CoA dehydratase (EC 4.2.1.-) (e.g., from *Clostridium viride*). See, e.g., FIG. 6.

In some embodiments, 2,4-pentadienoyl-CoA is synthesized from the central metabolite, L-glutamic acid, by conversion of L-glutamic acid to L-glutamyl-5-phosphate by a glutamate 5-kinase (EC 2.7.2.11); followed by conversion to L-glutamate-5-semialdehyde by a glutamate-5-semialdehyde dehydrogenase (EC 1.2.1.41); followed by spontaneous conversion to (S)-1-pyrroline-5-carboxylate; followed by conversion to L-proline by a pyrroline-5-carboxylate reductase (EC 1.5.1.2); followed by conversion to D-proline by a proline racemase (EC 5.1.1.4); followed by conversion to 5-aminovalerate by a D-proline reductase (EC 1.21.4.1); followed by conversion to 5-oxopentanoate by a 5-aminovalerate transaminase (EC 2.6.1.48); followed by conversion to 5-hydroxypentanoate by a 5-hydroxyvalerate dehydrogenase such as the gene product of cpnD or a dehydrogenase from *Clostridium viride*; followed by conversion to 5-hydroxypentanoyl-CoA by a 5-hydroxypentanoate CoA-transferase (EC 2.8.3.14); followed by conversion to 2,4-pentadienoyl-CoA by a 5-hydroxyvaleryl-CoA dehydratase (EC 4.2.1.-) (e.g., from *Clostridium viride*). See, e.g., FIG. 6.

In some embodiments, butadiene is synthesized from 2,4-pentadienoyl-CoA by conversion of 2,4-pentadienoyl-CoA to (R)-3-hydroxypent-4-enoyl-CoA by an enoyl-CoA dehydratase 2 (EC 4.2.1.119) such as the gene product of phaJ; followed by conversion to (R)-3-hydroxypent-4-enoate by a thioesterase such as the gene product of tesB; followed by conversion to butadiene by a mevalonate diphosphate decarboxylase (EC 4.1.1.33). See, e.g., FIG. 9.

The gene product of phaJ (EC 4.2.1.119) is a key enzyme for providing short and medium chain R-specific 3-hydroxyacyl-CoA monomers from fatty acid synthesis to polyhydroxyalkanoate synthase enzymes (Chung and Rhee, *Biosci. Biotechnol. Biochem.*, 2012, 76(3), 613-616; Tsuge et al., *International Journal of Biological Macromolecules*, 2003, 31, 195-205).

Utilizing 4-pentenoic acid as a carbon source to polyhydroxyalkanoate-producing bacteria produces (R)-3-hydroxypent-4-enoate via beta-oxidation. Accordingly, 4-pentenoic acid is converted to 2,4-pentadienoyl-CoA, which is made available to polymer synthase enzymes after hydration to (R)-3-hydroxypent-4-enoate by R-specific enoyl-CoA dehydrase activity (see, e.g., Ulmer et al., *Macromolecules*, 1994, 27, 1675-1679).

4.3.7 Pathway Using Crotonyl-CoA as Central Precursor to Butadiene

In some embodiments, crotonyl-CoA is synthesized from the central metabolite, acetyl-CoA, by conversion of acetyl-CoA to acetoacetyl-CoA by an acetyl-CoA C-acetyltransferase (EC 2.3.1.9) such as the gene product of atoB or phaA; followed by conversion to (R) 3-hydroxybutanoyl-CoA by a 3-hydroxybutyryl-CoA dehydrogenase (EC 1.1.1.36) such as the gene product of phaB; followed by conversion to crotonyl-CoA by an enoyl-CoA hydratase (EC 4.2.1.119) such as the gene product of phaJ. See, e.g., FIG. 7.

In some embodiments, crotonyl-CoA is synthesized from the central metabolite, succinyl-CoA, by conversion of succinyl-CoA to succinate semialdehyde by a succinate-semialdehyde dehydrogenase (EC 1.2.1.76); followed by conversion to 4-hydroxybutyrate by a 4-hydroxybutyrate dehydrogenase (EC 1.1.1.61); followed by conversion to 4-hydroxybutyryl-CoA by a CoA-transferase such as the gene product of Ck-cat2; followed by conversion to crotonyl-CoA by a 4-hydroxybutanoyl-CoA dehydratase (EC 4.2.1.120) and a vinylacetyl-CoA isomerase (EC 5.3.3.3). See, e.g., FIG. 7.

In some embodiments, crotonyl-CoA is synthesized from the central metabolite, 2-oxo-glutarate, by conversion of 2-oxo-glutarate to 2-hydroxyglutarate by a 2-hydroxyglutarate dehydrogenase (EC 1.1.99.2); followed by conversion to 2-hydroxyglutaryl-CoA by a glutaconate CoA-transferase (EC 2.8.3.12); followed by conversion to glutaconyl-CoA by a dehydrase (EC 4.2.1.-); followed by conversion to crotonyl-CoA by a glutaconyl-CoA decarboxylase (EC 4.1.1.70). See, e.g., FIG. 7.

In some embodiments, butadiene is synthesized from crotonyl-CoA by conversion to crotonic acid by a succinate-CoA ligase (EC 6.2.1.5); followed by conversion to 2-butenal by a long-chain-aldehyde dehydrogenase (EC 1.2.1.48); followed by conversion to 2-buten-1-ol by an allyl-alcohol dehydrogenase (EC 1.1.1.54); followed by conversion to 2-buten-1-ol phosphate by a mevalonate kinase (EC 2.7.1.36); followed by conversion to 2-buten-1-ol diphosphate by a phosphomevalonate kinase (EC 2.7.4.2); followed by conversion to butadiene by an isoprene synthase (EC 4.2.3.27). See, e.g., FIG. 10.

In some embodiments, butadiene is synthesized from crotonyl-CoA by conversion to crotonic acid by a succinate-CoA ligase (EC 6.2.1.5); followed by conversion to 2-butenal by a long-chain-aldehyde dehydrogenase (EC 1.2.1.48); followed by conversion to 2-buten-1-ol by an allyl-alcohol dehydrogenase (EC 1.1.1.54); followed by conversion to 2-buten-1-ol diphosphate by a diphosphotransferases such as a thiamine diphosphokinase (EC 2.7.6.2); followed by conversion to butadiene by an isoprene synthase (EC 4.2.3.27). See, e.g., FIG. 10.

In some embodiments, butadiene is synthesized from crotonyl-CoA by conversionof crotonyl-CoA to crotonic acid by a succinate-CoA ligase (EC 6.2.1.5); followed by conversion to 2-buten-al by a long-chain-aldehyde dehydrogenase (EC 1.2.1.48); followed by conversion to 2-buten-1-ol by an allyl-alcohol dehydrogenase (EC 1.1.1.54); followed by conversion to butadiene by a dehydratase in enzyme class EC 4.2.1.-, such as linalool dehydratase (EC 4.2.1.127), kievitone hydratase (EC 4.2.1.95), oleate hydratase (EC 4.2.1.53) or carotenoid 1,2-hydratase (EC 4.2.1.131). See, e.g., FIG. 11.

4.3.8 Pathway Using 3-buten-2-ol as Central Precursor to Butadiene

In some embodiments, 3-buten-2-ol is synthesized from the central metabolite, pyruvate, by conversion of pyruvate to 2-acetolactate by an acetolactate synthase (EC 2.2.1.6); followed by conversion to (R)-acetoin by an acetolactate decarboxylase (EC 4.1.1.5); followed by conversion to 2,3 butanediol by a (R,R)-butanediol dehydrogenase (EC 1.1.1.4); followed by conversion to butanone by a propanediol dehydratase (EC 4.2.1.28); followed by conversion to 2-butanol by a (R)-specific secondary alcohol dehydrogenase (EC 1.1.1.B4); followed by conversion to 3-buten-2-ol by a desaturase or a monooxygenase such as the gene product of MdpJ or cytochrome P450 in, for example, the CYP4 family. See, e.g., FIG. 8.

In some embodiments, butadiene is synthesized from 3-buten-2-ol by conversion to 3-buten-2-ol phosphate by a mevalonate kinase (EC 2.7.1.36); followed by conversion to 3-buten-2-ol diphosphate by a phosphomevalonate kinase (EC 2.7.4.2); followed by conversion to butadiene by an isoprene synthase (EC 4.2.3.27). See, e.g., FIG. 10.

In some embodiments, butadiene is synthesized from 3-buten-2-ol by conversion to 3-buten-2-ol diphosphate by a diphosphotransferases such as a thiamine diphosphokinase (EC 2.7.6.2); followed by conversion to butadiene by an isoprene synthase (EC 4.2.3.27). See, e.g., FIG. 10.

In some embodiments, butadiene is synthesized from 3-buten-2-ol by a dehydratase in enzyme class EC 4.2.1.-, such as a linalool dehydratase (EC 4.2.1.127), a kievitone hydratase (EC 4.2.1.95), an oleate hydratase (EC 4.2.1.53) or a carotenoid 1,2-hydratase (EC 4.2.1.131). See, e.g., FIG. 11.

4.4 Cultivation Strategy

In some embodiments, butadiene is biosynthesized in a recombinant host using a fermentation strategy that can include anaerobic, micro-aerobic or aerobic cultivation of the recombinant host.

Pathways in the synthesis of butadiene that incorporate enzymes requiring molecular oxygen and enzymes characterized in vitro as being oxygen sensitive require a micro-aerobic cultivation strategy maintaining a low dissolved oxygen concentration, whilst maintaining sufficient oxygen transfer to prevent substrate oxidation controlled conditions (Chayabatra & Lu-Kwang, *Appl. Environ. Microbiol.*, 2000, 66(2), 493 0 498).

In some embodiments, a cell retention strategy using, for example, ceramic hollow fiber membranes is employed to achieve and maintain a high cell density during either fed-batch or continuous fermentation in the synthesis of butadiene.

In some embodiments, the principal carbon source fed to the fermentation in the synthesis of butadiene derives from biological or non-biological feedstocks.

In some embodiments, the biological feedstock is, includes, or derives from, monosaccharides, disaccharides, lignocellulose, hemicellulose, cellulose, lignin such as levulinic acid and furfural, lignin, triglycerides such as glycerol and fatty acids, agricultural waste or municipal waste.

The efficient catabolism of crude glycerol stemming from the production of biodiesel has been demonstrated in several microorganisms such as *Escherichia coli, Cupriavidus necator, Pseudomonas oleavorans, Pseudomonas putida* and *Yarrowia lipolytica* (Lee et al., *Appl. Biochem. Biotechnol.*, 2012, 166, 1801-1813; Yang et al., Bio*technology for Biofuels*, 2012, 5:13; Meijnen et al., *Appl. Microbiol. Biotechnol.*, 2011, 90, 885-893).

The efficient catabolism of lignocellulosic-derived levulinic acid has been demonstrated in several organisms such as *Cupriavidus necator* and *Pseudomonas putida* in the synthesis of 3-hydroxyvalerate via the precursor propanoyl-CoA (Jaremko and Yu, *Journal of Biotechnology*, 2011, 155, 2011, 293-298; Martin and Prather, *Journal of Biotechnology*, 2009, 139, 61-67).

The efficient catabolism of lignin-derived aromatic compounds such benzoate analogues has been demonstrated in several microorganisms such as *Pseudomonas putida, Cupriavidus necator* (Bugg et al., *Current Opinion in Biotechnology*, 2011, 22, 394-400; Perez-Pantoja et al., *FEMS Microbiol. Rev.*, 2008, 32, 736-794).

The efficient utilization of agricultural waste, such as olive mill waste water has been demonstrated in several microorganisms, including *Yarrowia lipolytica* (Papanikolaou et al., *Bioresour. Technol.*, 2008, 99(7), 2419-2428).

The efficient utilization of fermentable sugars such as monosaccharides and disaccharides derived from cellulosic, hemicellulosic, cane and beet molasses, cassava, corn and other argricultural sources has been demonstrated for several microorganism such as *Escherichia coli, Corynebacterium glutamicum* and *Lactobacillus delbrueckii* and *Lactococcus lactis* (see, e.g., Hermann et al., *Journal of Biotechnology*, 2003, 104, 155-172; Wee et al., *Food Technol. Biotechnol.*, 2006, 44(2), 163-172; Ohashi et al., *Journal of Bioscience and Bioengineering*, 1999, 87(5), 647-654).

The efficient utilization of furfural, derived from a variety of agricultural lignocellulosic sources, has been demonstrated for *Cupriavidus necator* (Li et al., *Biodegradation*, 2011, 22, 1215-1225).

In some embodiments, the non-biological feedstock is or derives from natural gas, syngas, $CO_2/H_2$, methanol, ethanol, non-volatile residue (NVR) or a caustic wash waste stream from cyclohexane oxidation processes.

The efficient catabolism of methanol has been demonstrated for the methylotropic yeast *Pichia pastoris*.

The efficient catabolism of ethanol has been demonstrated for *Clostridium kluyveri* (Seedorf et al., *Proc. Natl. Acad. Sci. USA*, 2008, 105(6) 2128-2133).

The efficient catabolism of $CO_2$ and $H_2$, which may be derived from natural gas and other chemical and petrochemical sources, has been demonstrated for *Cupriavidus necator* (Prybylski et al., *Energy, Sustainability and Society*, 2012, 2:11).

The efficient catabolism of syngas has been demonstrated for numerous microorganisms, such as *Clostridium ljungdahlii* and *Clostridium autoethanogenum* (Kopke et al., *Applied and Environmental Microbiology*, 2011, 77(15), 5467-5475).

The efficient catabolism of the non-volatile residue waste stream from cyclohexane processes has been demonstrated for numerous microorganisms, such as *Delftia acidovorans* and *Cupriavidus necator* (Ramsay et al., *Applied and Environmental Microbiology*, 1986, 52(1), 152-156).

In some embodiments, the host microorganism is a prokaryote. For example, the prokaryote can be from the genus *Escherichia* such as *Escherichia coli*; from the genus *Clostridia* such as *Clostridium ljungdahlii, Clostridium autoethanogenum* or *Clostridium kluyveri*; from the genus *Corynebacteria* such as *Corynebacterium glutamicum*; from the genus *Cupriavidus* such as *Cupriavidus necator* or *Cupriavidus metallidurans*; from the genus *Pseudomonas* such as *Pseudomonas fluorescens, Pseudomonas putida* or *Pseudomonas oleavorans*; from the genus *Delftia* such as *Delftia acidovorans*; from the genus *Bacillus* such as *Bacillus subtillis*; from the genus *Lactobacillus* such as *Lacto-*

*bacillus delbrueckii*; or from the genus *Lactococcus* such as *Lactococcus lactis*. Such prokaryotes also can be a source of genes to construct recombinant host cells described herein that are capable of producing butadiene.

In some embodiments, the host microorganism is a eukaryote. For example, the eukaryote can be from the genus *Aspergillus* such as *Aspergillus niger*; from the genus *Saccharomyces* such as *Saccharomyces cerevisiae*; from the genus *Pichia* such as *Pichia pastoris*; or from the genus *Yarrowia* such as *Yarrowia lipolytica*; from the genus *Issatchenkia* such as *Issathenkia orientalis*; from the genus *Debaryomyces* such as *Debaryomyces hansenii*; from the genus *Arxula* such as *Arxula adenoinivorans*; or from the genus *Kluyveromyces* such as *Kluyveromyces lactis*. Such eukaryotes also can be a source of genes to construct recombinant host cells described herein that are capable of producing butadiene.

4.5 Metabolic Engineering

The present document provides methods involving less than all the steps described for all the above pathways. Such methods can involve, for example, one, two, three, four, five, six, seven, eight, nine, ten, or more of such steps. Where less than all the steps are included in such a method, the first step can be any one of the steps listed.

Furthermore, recombinant hosts described herein can include any combination of the above enzymes such that one or more of the steps, e.g., one, two, three, four, five, six, seven, eight, nine, ten, or more of such steps, can be performed within a recombinant host.

In addition, this document recognizes that where enzymes have been described as accepting CoA-activated substrates, analogous enzyme activities associated with [acp]-bound substrates exist that are not necessarily in the same enzyme class.

Also, this document recognizes that where enzymes have been described accepting (R)-enantiomers of substrate, analogous enzyme activities associated with (S)-enantiomer substrates exist that are not necessarily in the same enzyme class.

This document also recognizes that where an enzyme is shown to accept a particular co-factor, such as NADPH, or co-substrate, such as acetyl-CoA, many enzymes are promiscuous in terms of accepting a number of different co-factors or co-substrates in catalyzing a particular enzyme activity. Also, this document recognizes that where enzymes have high specificity for e.g., a particular co-factor such as NADH, an enzyme with similar or identical activity that has high specificity for the co-factor NADPH may be in a different enzyme class.

In some embodiments, the enzymes in the pathways outlined in section 4.3 are the result of enzyme engineering via non-direct or rational enzyme design approaches with aims of improving activity, improving specificity, reducing feedback inhibition, reducing repression, improving enzyme solubility, changing stereo-specificity, or changing co-factor specificity.

In some embodiments, the enzymes in the pathways outlined in section 4.3 are gene dosed, i.e., overexpressed, into the resulting genetically modified organism via episomal or chromosomal integration approaches.

In some embodiments, genome-scale system biology techniques such as Flux Balance Analysis are utilized to devise genome scale attenuation or knockout strategies for directing carbon flux to butadiene.

Attenuation strategies include, but are not limited to; the use of transposons, homologous recombination (double cross-over approach), mutagenesis, enzyme inhibitors and RNAi interference.

In some embodiments, fluxomic, metabolomic and transcriptomal data are utilized to inform or support genome-scale system biology techniques, thereby devising genome scale attenuation or knockout strategies in directing carbon flux to butadiene.

In some embodiments requiring intracellular availability of propanoyl-CoA or propenoyl-CoA for butadiene synthesis, enzymes catalyzing the hydrolysis of propionyl-CoA and acetyl-CoA can be attenuated in the host organism.

In some embodiments requiring the intracellular availability of propanoyl-CoA or propenoyl-CoA for butadiene synthesis, enzymes consuming propanoyl-CoA via the methyl-citrate cycle are attenuated in the host organism (Upton and Mckinney, *Microbiology*, 2007, 153, 3973-3982).

In some embodiments requiring the intracellular availability of propanoyl-CoA or propenoyl-CoA for butadiene synthesis, enzymes consuming propanoyl-CoA to pyruvate are attenuated in the host organism.

In some embodiments requiring the intracellular availability of propanoyl-CoA or propenoyl-CoA for butadiene synthesis, enzymes consuming propanoyl-CoA to malonyl-CoA are attenuated in the host organism.

In some embodiments requiring the intracellular availability of propanoyl-CoA or propenoyl-CoA via L-threonine as central metabolite for butadiene synthesis, a feedback-resistant threonine deaminase is genetically engineered into the host organism (Tseng et al., *Microbial Cell Factories*, 2010, 9:96).

In some embodiments requiring condensation of acetyl-CoA and propanoyl-CoA/propenoyl-CoA for butadiene synthesis, the β-ketothiolases catalyzing the condensation of acetyl-CoA to acetoacetyl-CoA such as the gene products of AtoB or phaA can be attenuated.

In some embodiments using hosts that naturally accumulate polyhydroxyalkanoates, the polymer synthase enzymes can be attenuated in the host strain.

In some embodiments requiring the intracellular availability of acetyl-CoA for butadiene synthesis, a host that is deficient (e.g., attenuated level of activity) in one or more enzymes in the acetate synthesis pathway can be used. For example, a host that is deficient in a phosphotransacetylase (encoded by the pta gene) can be used (Shen et al., *Appi. Environ. Microbio.*, 2011, 77(9), 2905-2915).

In some embodiments requiring the intracellular availability of acetyl-CoA for butadiene synthesis, a gene in an acetate synthesis pathway encoding an acetate kinase, such as ack, is attenuated.

In some embodiments requiring the intracellular availability of acetyl-CoA for butadiene synthesis, a gene encoding the degradation of pyruvate to lactate such as ldhA is attenuated (Shen et al., *Appi. Environ. Microbio.*, 2011, 77(9), 2905-2915).

In some embodiments requiring the intracellular availability of acetyl-CoA for butadiene synthesis, a gene encoding the degradation of phophoenolpyruvate to succinate such as frdBC is attenuated (see, e.g., Shen et al., 2011, supra).

In some embodiments requiring the intracellular availability of acetyl-CoA for butadiene synthesis, a gene encoding the degradation of acetyl-CoA to ethanol such as adhE is attenuated (Shen et al., 2011, supra).

In some embodiments requiring the intracellular availability of L-glutamate for butadiene synthesis, the enzymes catalyzing anaplerotic reactions supplementing the citric acid cycle intermediates are amplified.

In some embodiments using MDD to enzymatically form the second vinyl group into butadiene, the thioesterase II gene product of tesB hydrolyses (R)-3-hydroxypent-4-enoyl-CoA to (R)-3-hydroxypent-4-enoate.

In some embodiments, where pathways require excess NADPH co-factor in the synthesis of butadiene, a puridine nucleotide transhydrogenase gene such as UdhA is overexpressed in the host organisms (Brigham et al., *Advanced Biofuels and Bioproducts,* 2012, Chapter 39, 1065-1090).

In some embodiments, where pathways require excess NADPH co-factor in the synthesis of butadiene, a glyceraldehyde-3P-dehydrogenase gene such as GapN is overexpressed in the host organisms (Brigham et al., 2012, supra).

In some embodiments, where pathways require excess NADPH co-factor in the synthesis of butadiene, a malic enzyme gene such as maeA or maeB is overexpressed in the host organisms (Brigham et al., 2012, supra).

In some embodiments, where pathways require excess NADPH co-factor in the synthesis of butadiene, a glucose-6-phosphate dehydrogenase gene such as zwf is overexpressed in the host organisms (Lim et al., *Journal of Bioscience and Bioengineering,* 2002, 93(6), 543-549).

In some embodiments, where pathways require excess NADPH co-factor in the synthesis of butadiene, a fructose 1,6 diphosphatase gene such as fbp is overexpressed in the host organisms (Becker et al., *Journal of Biotechnology,* 2007, 132, 99-109).

In some embodiments, the efflux of butadiene across the cell membrane to the extracellular media is enhanced or amplified by genetically engineering structural modifications to the cell membrane or increasing any associated transporter activity for butadiene.

In some embodiments, oxygenases degrading butadiene to toxic intermediates such as 1,2-epoxy-3-butene and 1,2:3,4-diepoxybutane are attenuated in the host organism (see, e.g., Sweeney et al., *Carcinogenesis,* 1997, 18(4), 611-625).

The invention will be further described in the following examples, which do not limit the scope of the invention described in the claims.

EXAMPLES

Example 1

Enzyme Activity of Mevalonate Diphosphate Decarboxylase Accepting 3-Hydroxypent-4-Enoic Acid as Substrate The his-tagged MDD genes from *Saccharomyces cerevisiae, Staphyloccocus epidermidis* and *Streptococcus pneumonia* were cloned and expressed in *E. coli* in a shake flask culture containing Luria Broth media.

The pellet from each of the induced shake flask cultures was harvested by centrifugation, and then the pellet was resuspended and lysed. The cell debris was separated from the supernatant via centrifugation and filtered using a 0.2 µm filter. The MDD enzymes were purified from the supernatant using Ni-affinity chromatography, concentrated and buffer exchanged via ultrafiltration into 50 mM Tris buffer (pH=7.5), 100 mM NaCl, and 5% (v/v) glycerol using a 10 kDa polyethersulfone membrane.

Native enzyme activity was confirmed in a buffer composed of 50 mM Tris-HCl (pH=7.5), 100 mM NaCl, 5% (v/v) glycerol, 10 mM $MgCl_2$, 15 mM ATP and 5 mM of the native substrate mevalonate diphosphate (from Sigma Aldrich) at 30° C. The enzyme activity assay reaction was initiated by adding 10 µL of each purified MDD enzyme to the assay buffer containing the substrate. All three MDD enzymes accepted mevalonate diphosphate as substrate as confirmed via LC-MS.

Non-native enzyme activity assays were undertaken in a buffer composed of 50 mM Tris HCl (pH=7.5), 100 mM NaCl, 5% (v/v) glycerol, 10 mM $MgCl_2$, 15 mM ATP and 4 mM of the non-native racemic substrate, 3-hydroxypent-4-enoic acid (purity >95%, from Epison Chimie) at 30° C. Non-native activity assay were undertaken in 2 mL septum-sealed vials, thereby allowing butadiene accumulation in the headspace. The reaction was initiated by adding 10 µL of each purified MDD enzyme variant to the assay buffer containing the substrate.

The three MDD enzymes from *Saccharomyces cerevisiae, Staphyloccocus epidermidis* and *Streptococcus pneumonia* had similar chromatograms and spectra for non-native enzyme activity assays using 3-hydroxypent-4-enoic acid as substrate.

The retention time for the butadiene standard and the assay samples were within 2%. The ratio of the MS ion peak areas from the butadiene standard and the MS ion peak areas of the samples agree to within 20%. Also, the ion peak areas were above the limit of quantitation for the GC/MS.

The MDD enzymes from *Saccharomyces cerevisiae, Staphyloccocus epidermidis* and *Streptococcus pneumonia* accepted 3-hydroxypent-4-enoic acid as substrate, synthesizing butadiene.

Example 2

Amino Acid Residues Increasing the Activity of Mevalonate Diphosphate Decarboxylase in Accepting 3-Hydroxypent-4-Enoic Acid as Substrate FIG. 13 provides the amino acid sequences for the MDD enzymes from *Saccharomyces cerevisiae, Staphyloccocus epidermidis* and *Streptococcus pneumonia,* with the conserved residues within the catalytic cleft of the enzyme in bold.

Using the total protein concentration and the purity from densitometry, the enzyme concentration for the purified MDD from *S. cerevisiae* was 385 µg/mL and for the purified MDD from *S. pneumonia,* it was 88 µg/mL.

Given the incomplete conversion of 3-hydroxypent-4-enoic acid as non-native substrate, the specific conversion of MDD from *S. cerevisiae* was 809 [(peak area for m/z 54 ion)/(µg MDD)] and MDD from *S. pneumonia*'s was 3200 [(peak area for m/z 54 ion)/(µg MDD)]. The specific conversion of MDD from *S. pneumonia* is thus approximately four times greater than the specific conversion of MDD from *S. cerevisiae.* The specific conversion of MDD from *S. epidermidis* lies between the specific conversions of MDD from *S. pneumonia* and *S. cerevisiae* (not calculated).

The amino acid residues in the region of the catalytic arginine residue at R158 in *S. cerevisiae,* R144 in *S. epidermidis* and R144 in *S. pneumonia* reveal a trend of increasing serine density within 5 amino acid residues. R158 in *S. cerevisiae* has 3 serine residues within 5 amino acid residues (residues 153, 155, and 159), R144 in *S. epidermidis* has 4 serine residues within 5 amino acid residues (residues 139, 141, 143, and 145) and R144 in *S. pneumonia* has 5 serine residues within 5 amino acid residues (residues 139, 141, 142, 143, and 145). See, e.g, FIG. 13.

MDD's activity in accepting 3-hydroxypent-4-enoic acid as non-native substrate increases as the serine density increases within the region of the catalytic arginine residue of the catalytic cleft.

Example 3

Enzyme Activity of Isoprene Synthase Accepting Trans-2-Butenylpyrophosphate as Substrate The his-tagged isoprene synthase (ISPS) gene from *Populus alba* was cloned and expressed in *E. coli* in a shake flask culture containing Luria Broth media.

The pellet from each of the induced shake flask cultures was harvested by centrifugation, and then the pellet was resuspended and lysed. The cell debris was separated from the supernatant via centrifugation and filtered through a 0.2 μm filter. The ISPS enzyme variants were purified from the supernatant using Ni-affinity chromatography, concentrated and buffer exchanged into 50 mM Tris buffer (pH=7.5), 100 mM NaCl and 5% (v/v) glycerol using a 10 kDa polyethersulfone membrane.

Native enzyme activity was confirmed in a buffer composed of 50 mM Tris.HCl (pH=7.5), 100 mM NaCl, 5% (v/v) glycerol, 20 mM $MgCl_2$ and 5 mM of the native substrate, dimethylallyl diphosphate from Sigma-Aldrich, at 30° C. The native activity assay was undertaken in 2 mL septum-sealed vials, thereby allowing isoprene accumulation in the headspace. The enzyme activity assay reaction was initiated by adding 10 μL of each purified ISPS enzyme to the assay buffer containing the substrate. ISPS from *P. alba* accepted dimethylallyl diphosphate as substrate as confirmed via GC-MS.

Non-native enzyme activity assays were undertaken in a buffer composed of 50 mM Tris.HCl (pH=7.5), 100 mM NaCl, 5% (v/v) glycerol, 20 mM $MgCl_2$ and 5 mM of the non-native substrate, trans-2-butenylpyrophosphate (purity >90%) from DALTON Pharma Services, at 30° C. Non-native activity assay were undertaken in 2 mL septum-sealed vials, thereby allowing butadiene accumulation in the headspace. The enzyme activity assay reaction was initiated by adding 10 μL of the purified ISPS enzyme to the assay buffer containing the substrate.

The retention time for the butadiene standard and the assay samples are within 2%. The ratio of the MS ion peak areas from the butadiene standard and the MS ion peak areas of the samples agree to within 20%. Also, the ion peak areas were above the limit of quantitation for the GC/MS.

The ISPS enzymes from *Populus alba* accepted trans-2-butenylpyrophosphate as substrate, synthesising butadiene.

Example 4

Enzyme Activity of Linalool Dehydratase Using 3-Buten-2-ol as Substrate

The his-tagged linalool dehydratase (EC 4.2.1.127) from *Castellaniella defragrans* was cloned into a pARZ4 vector and transformed into *E. coli* BL21. The resulting strain was cultivated and induced using 1 [M] IPTG (isopropylthio-β-galactoside) in a shake flask culture containing Luria Broth media and kanamycin selection pressure.

The cells from each of the induced shake flask cultures were harvested and pelleted by centrifugation. The cell pellet was resuspended and the cells were lysed. The cell debris was separated from the supernatant via centrifugation and filtered using a 0.2 μm filter. The enzyme was purified from the filtered supernatant using Ni-affinity chromatography and concentrated and buffer exchanged using a Vivaspin 15R Centrifugal Concentrator and Hi-trap Desalting column into 80 mM Tris buffer (pH=9).

Non-native enzyme activity assays were undertaken in a buffer containing 11 mM of 3-buten-2-ol at 25° C. The activity assays were undertaken in 2 mL septum-sealed vials, thereby allowing butadiene accumulation in the headspace. The reaction was initiated by adding 1 mL of purified enzyme to the assay buffer containing the substrate.

The headspace was sampled for butadiene analysis by GC-MS (gas chromatography-mass spectrometry). The retention time for the butadiene standard and the assay samples were within 2%. The ratio of the MS ion peak areas from the butadiene standard and the MS ion peak areas of the samples agree to within 20%. Also, the ion peak areas were above the limit of quantitation for the GC-MS.

These findings show that linalool dehydratase (EC 4.2.1.127) accepts 3-buten-2-ol as a substrate, thereby synthesizing butadiene.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for the biosynthesis of butadiene comprising converting a butanol or butene to 3-buten-2-ol using (a) a polypeptide having the activity of a desaturase or (b) using a polypeptide having the activity of a monooxygenase to form a first terminal vinyl group, wherein said desaturase or monooxygenase forms a first vinyl group, and wherein said desaturase is a cytochrome P450 or said monooxygenase is a gene product of mdpJ, and forming a second terminal vinyl group in the 3-buten-2-ol using a polypeptide having the activity of a dehydratase in enzyme class EC 4.2.1 capable of accepting a hydroxylated substrate to biosynthesize butadiene.

2. The method of claim 1 wherein said method is performed using isolated enzymes.

3. The method of claim 1, wherein said method is performed using cell lysates comprising enzymes.

4. The method of claim 1, wherein said method is performed in a recombinant host.

5. The method of claim 4, wherein the recombinant host is anaerobically, micro-aerobically or aerobically cultivated by fermentation.

6. The method according to claim 5, wherein the cells of said recombinant host are retained in ceramic hollow fibre membranes to maintain a high cell density during fermentation.

7. The method of 5, wherein the principal carbon source fed to the fermentation derives from biological or non-biological feedstocks.

8. The method of 7, wherein the biological feedstock is or derives from monosaccharides, disaccharides, lignocellulose, hemicellulose, cellulose, lignin, agricultural waste or municipal waste.

9. The method of claim 7, wherein the non-biological feedstock is or derives from either natural gas, syngas, $CO_2/H_2$, methanol, ethanol, non-volatile residue (NVR) or caustic wash waste stream from cyclohexane oxidation processes.

10. The method of claim 4, wherein the recombinant host is a prokaryote or an eukaryote.

11. The method of claim 10, wherein the recombinant host is a prokaryote from a genus selected from the group consisting of *Escherichia* from the genus *Clostridia*, *Corynebacteria*, *Cupriavidus*, *Pseudomonas*, *Delftia*, *Bacillus*, *Lactobacillus* and *Lactococcus*.

12. The method of claim 10, wherein the recombinant host is a eukaryote from a genus selected from the group consisting of *Aspergillus, Saccharomyces, Pichia, Yarrowia, Issatchenkia, Debaryomyces, Arxula,* and *Kluyveromyces.*

13. The method of claim 4, wherein enzymes catalyzing the hydrolysis of propionyl-CoA and acetyl-CoA are attenuated in the host organism, enzymes consuming propanoyl-CoA via the methyl-citrate cycle are attenuated in the host organism, enzymes consuming propanoyl-CoA to pyruvate are attenuated in the host organism, or enzymes consuming propanoyl-CoA to malonyl-CoA are attenuated in the host organism.

14. The method of claim 4, wherein a feedback-resistant threonine deaminase is genetically engineered into the recombinant host organism.

15. The method of claim 4, wherein β-ketothiolases catalysing the condensation of acetyl-CoA to acetoacetyl-CoA are attenuated.

16. The method of claim 4, wherein polymer synthase enzymes in a host strain that naturally accumulates polyhydroxyalkanoates are attenuated.

17. The method of claim 4, wherein a gene encoding a phosphotransacetylase is attenuated, a gene encoding an acetate kinase degrading propanoate is attenuated, a gene encoding the degradation of pyruvate to lactate is attenuated, a gene encoding the degradation of phosphoenolpyruvate to succinate is attenuated, or a gene encoding the degradation of acetyl-CoA to ethanol is attenuated.

18. The method according to claim 4, wherein enzymes catalysing anaplerotic reactions supplementing the citric acid cycle intermediates are amplified.

19. The method of claim 4, wherein a puridine nucleotide transhydrogenase gene is overexpressed in the recombinant host organism, a glyceraldehyde-3P-dehydrogenase gene is overexpressed in the recombinant host organism, a malic enzyme gene is overexpressed in the recombinant host organism, a glucose-6-phosphate dehydrogenase gene is overexpressed in the recombinant host organism, or a fructose 1,6 diphosphatase gene is overexpressed in the recombinant host organism.

20. The method of claim 4, wherein the efflux of butadiene across the cell membrane to the extracellular media is enhanced or amplified by genetically engineering structural modifications to the cell membrane.

21. The method of claim 4, wherein the efflux of butadiene across the cell membrane to the extracellular media is enhanced or amplified by genetically engineering an increase to any associated transporter activity for butadiene.

22. The method according to claim 2, wherein oxygenases degrading butadiene to toxic intermediates are attenuated in the recombinant host organism.

23. The method of claim 11, wherein the recombinant host is selected from the group consisting of *Escherichia coli, Clostridium ljungdahlii, Clostridium autoethanogenum, Clostridium kluyveri, Corynebacterium glutamicum, Cupriavidus necator, Cupriavidus metallidurans, Pseudomonas fluorescens, Pseudomonas putida, Pseudomonas oleavorans, Delftia acidovorans, Bacillus subtillis, Lactobacillus delbrueckii,* and *Lactococcus lactis.*

24. The method of claim 12, wherein the recombinant host is selected from the group consisting of *Aspergillus niger, Saccharomyces cerevisiae, Pichia pastoris, Yarrowia lipolytica, Issathenkia orientalis, Debaryomyces hansenii, Arxula adenoinivorans,* and *Kluyveromyces lactis.*

25. The method of claim 15, wherein the-β-ketothiolases are the gene products of AtoB or phaA.

26. The method of claim 17, wherein the phosphotransacetylase is pta.

27. The method of claim 17, wherein the acetate kinase is ack.

28. The method of claim 17, wherein the gene encoding the degradation of phosphoenolpyruvate to succinate is frdBC.

29. The method of claim 17, wherein the gene encoding the degradation of acetyl-CoA to ethanol is adhE.

30. The method of claim 19, wherein the puridine nucleotide transhydrogenase gene is UdhA.

31. The method of claim 19, wherein the glyceraldehyde-3P-dehydrogenase gene is GapN.

32. The method of claim 19, wherein the malic enzyme gene is maeA or maeB.

33. The method of claim 19, wherein the glucose-6-phosphate dehydrogenase gene is zwf.

34. The method of claim 19, wherein the fructose 1,6 diphosphatase gene is fbp.

35. The method of claim 22, wherein the toxic intermediates are 1,2-epoxy-3-butene or 1,2:3,4-diepoxybutane.

* * * * *

SEQUENCE LISTING

<160> NUMBER OF SEQ ID NOS: 3

<210> SEQ ID NO 1
<211> LENGTH: 396
<212> TYPE: PRT
<213> ORGANISM: Saccharomyces cerevisiae

<400> SEQUENCE: 1

Met Thr Val Tyr Thr Ala Ser Val Thr Ala Pro Val Asn Ile Ala Thr
1               5                   10                  15

Leu Lys Tyr Trp Gly Lys Arg Asp Thr Lys Leu Asn Leu Pro Thr Asn
            20                  25                  30

Ser Ser Ile Ser Val Thr Leu Ser Gln Asp Asp Leu Arg Thr Leu Thr
        35                  40                  45

Ser Ala Ala Thr Ala Pro Glu Phe Glu Arg Asp Thr Leu Trp Leu Asn
 50                  55                  60

Gly Glu Pro His Ser Ile Asp Asn Glu Arg Thr Gln Asn Cys Leu Arg
 65                  70                  75                  80

Asp Leu Arg Gln Leu Arg Lys Glu Met Glu Ser Lys Asp Ala Ser Leu
                 85                  90                  95

Pro Thr Leu Ser Gln Trp Lys Leu His Ile Val Ser Glu Asn Asn Phe
            100                 105                 110

Pro Thr Ala Ala Gly Leu Ala Ser Ala Ala Gly Phe Ala Ala Leu
            115                 120                 125

Val Ser Ala Ile Ala Lys Leu Tyr Gln Leu Pro Gln Ser Thr Ser Glu
130                 135                 140

Ile Ser Arg Ile Ala Arg Lys Gly Ser Gly Ser Ala Cys Arg Ser Leu
145                 150                 155                 160

Phe Gly Gly Tyr Val Ala Trp Glu Met Gly Lys Ala Glu Asp Gly His
                165                 170                 175

Asp Ser Met Ala Val Gln Ile Ala Asp Ser Ser Asp Trp Pro Gln Met
            180                 185                 190

Lys Ala Cys Val Leu Val Val Ser Asp Ile Lys Lys Asp Val Ser Ser
            195                 200                 205

Thr Gln Gly Met Gln Leu Thr Val Ala Thr Ser Glu Leu Phe Lys Glu
210                 215                 220

Arg Ile Glu His Val Val Pro Lys Arg Phe Glu Val Met Arg Lys Ala
225                 230                 235                 240

Ile Val Glu Lys Asp Phe Ala Thr Phe Ala Lys Glu Thr Met Met Asp
                245                 250                 255

Ser Asn Ser Phe His Ala Thr Cys Leu Asp Ser Phe Pro Pro Ile Phe
            260                 265                 270

Tyr Met Asn Asp Thr Ser Lys Arg Ile Ile Ser Trp Cys His Thr Ile
            275                 280                 285

Asn Gln Phe Tyr Gly Glu Thr Ile Val Ala Tyr Thr Phe Asp Ala Gly
290                 295                 300

Pro Asn Ala Val Leu Tyr Tyr Leu Ala Glu Asn Glu Ser Lys Leu Phe
305                 310                 315                 320

Ala Phe Ile Tyr Lys Leu Phe Gly Ser Val Pro Gly Trp Asp Lys Lys
                325                 330                 335

Phe Thr Thr Glu Gln Leu Glu Ala Phe Asn His Gln Phe Glu Ser Ser
            340                 345                 350

Asn Phe Thr Ala Arg Glu Leu Asp Leu Glu Leu Gln Lys Asp Val Ala
            355                 360                 365

Arg Val Ile Leu Thr Gln Val Gly Ser Gly Pro Gln Glu Thr Asn Glu
370                 375                 380

Ser Leu Ile Asp Ala Lys Thr Gly Leu Pro Lys Glu
385                 390                 395

<210> SEQ ID NO 2
<211> LENGTH: 327
<212> TYPE: PRT
<213> ORGANISM: Staphylococcus epidermidis

<400> SEQUENCE: 2

Met Val Lys Ser Gly Lys Ala Arg Ala His Thr Asn Ile Ala Leu Ile
 1               5                  10                  15

Lys Tyr Trp Gly Lys Ala Asp Glu Thr Tyr Ile Ile Pro Met Asn Asn

```
            20                  25                  30
Ser Leu Ser Val Thr Leu Asp Arg Phe Tyr Thr Glu Thr Lys Val Thr
                35                  40                  45
Phe Asp Pro Asp Phe Thr Glu Asp Cys Leu Ile Leu Asn Gly Asn Glu
 50                  55                  60
Val Asn Ala Lys Glu Lys Glu Lys Ile Gln Asn Tyr Met Asn Ile Val
 65                  70                  75                  80
Arg Asp Leu Ala Gly Asn Arg Leu His Ala Arg Ile Glu Ser Glu Asn
                85                  90                  95
Tyr Val Pro Thr Ala Ala Gly Leu Ala Ser Ala Ser Ala Tyr Ala
                100                 105                 110
Ala Leu Ala Ala Ala Cys Asn Glu Ala Leu Ser Leu Asn Leu Ser Asp
                115                 120                 125
Thr Asp Leu Ser Arg Leu Ala Arg Arg Gly Ser Gly Ser Ala Ser Arg
                130                 135                 140
Ser Ile Phe Gly Gly Phe Ala Glu Trp Glu Lys Gly His Asp Asp Leu
145                 150                 155                 160
Thr Ser Tyr Ala His Gly Ile Asn Ser Asn Gly Trp Glu Lys Asp Leu
                165                 170                 175
Ser Met Ile Phe Val Ile Asn Asn Gln Ser Lys Lys Val Ser Ser
                180                 185                 190
Arg Ser Gly Met Ser Leu Thr Arg Asp Thr Ser Arg Phe Tyr Gln Tyr
                195                 200                 205
Trp Leu Asp His Val Asp Glu Asp Leu Asn Glu Ala Lys Glu Ala Val
                210                 215                 220
Lys Asn Gln Asp Phe Gln Arg Leu Gly Glu Val Ile Glu Ala Asn Gly
225                 230                 235                 240
Leu Arg Met His Ala Thr Asn Leu Gly Ala Gln Pro Pro Phe Thr Tyr
                245                 250                 255
Leu Val Gln Glu Ser Tyr Asp Ala Met Ala Ile Val Glu Gln Cys Arg
                260                 265                 270
Lys Ala Asn Leu Pro Cys Tyr Phe Thr Met Asp Ala Gly Pro Asn Val
                275                 280                 285
Lys Val Leu Val Glu Lys Lys Asn Lys Gln Ala Val Met Glu Gln Phe
                290                 295                 300
Leu Lys Val Phe Asp Glu Ser Lys Ile Ile Ala Ser Asp Ile Ile Ser
305                 310                 315                 320
Ser Gly Val Glu Ile Ile Lys
                325

<210> SEQ ID NO 3
<211> LENGTH: 317
<212> TYPE: PRT
<213> ORGANISM: Streptococcus pneumonia

<400> SEQUENCE: 3

Met Asp Arg Glu Pro Val Thr Val Arg Ser Tyr Ala Asn Ile Ala Ile
 1                   5                  10                  15

Ile Lys Tyr Trp Gly Lys Lys Glu Lys Glu Met Val Pro Ala Thr
                20                  25                  30

Ser Ser Ile Ser Leu Thr Leu Glu Asn Met Tyr Thr Glu Thr Thr Leu
                35                  40                  45

Ser Pro Leu Pro Ala Asn Val Thr Ala Asp Glu Phe Tyr Ile Asn Gly
 50                  55                  60
```

-continued

```
Gln Leu Gln Asn Glu Val Glu His Ala Lys Met Ser Lys Ile Ile Asp
 65              70                  75                      80

Arg Tyr Arg Pro Ala Gly Glu Gly Phe Val Arg Ile Asp Thr Gln Asn
             85                  90                  95

Asn Met Pro Thr Ala Ala Gly Leu Ser Ser Ser Ser Ser Gly Leu Ser
            100                 105                 110

Ala Leu Val Lys Ala Cys Asn Ala Tyr Phe Lys Leu Gly Leu Asp Arg
            115                 120                 125

Ser Gln Leu Ala Gln Glu Ala Lys Phe Ala Ser Gly Ser Ser Ser Arg
130                 135                 140

Ser Phe Tyr Gly Pro Leu Gly Ala Trp Asp Lys Asp Ser Gly Glu Ile
145                 150                 155                 160

Tyr Pro Val Glu Thr Asp Leu Lys Leu Ala Met Ile Met Leu Val Leu
            165                 170                 175

Glu Asp Lys Lys Lys Pro Ile Ser Ser Arg Asp Gly Met Lys Leu Cys
            180                 185                 190

Val Glu Thr Ser Thr Thr Phe Asp Asp Trp Val Arg Gln Ser Glu Lys
        195                 200                 205

Asp Tyr Gln Asp Met Leu Ile Tyr Leu Lys Glu Asn Asp Phe Ala Lys
        210                 215                 220

Ile Gly Glu Leu Thr Glu Lys Asn Ala Leu Ala Met His Ala Thr Thr
225                 230                 235                 240

Lys Thr Ala Ser Pro Ala Phe Ser Tyr Leu Thr Asp Ala Ser Tyr Glu
            245                 250                 255

Ala Met Asp Phe Val Arg Gln Leu Arg Glu Lys Gly Glu Ala Cys Tyr
            260                 265                 270

Phe Thr Met Asp Ala Gly Pro Asn Val Lys Val Phe Cys Gln Glu Lys
        275                 280                 285

Asp Leu Glu His Leu Ser Glu Ile Phe Gly His Arg Tyr Arg Leu Ile
        290                 295                 300

Val Ser Lys Thr Lys Asp Leu Ser Gln Asp Asp Cys Cys
305                 310                 315
```